US008116883B2

(12) United States Patent
Williams et al.

(10) Patent No.: US 8,116,883 B2
(45) Date of Patent: Feb. 14, 2012

(54) INTRAVASCULAR DEVICE FOR NEUROMODULATION

(75) Inventors: Michael S. Williams, Santa Rosa, CA (US); Richard S. Stack, Chapel Hill, NC (US); Lynn Elliott, Maple Grove, MN (US); Colleen Stack N'diaye, Hillsborough, NC (US); Daniel W. Fifer, Windsor, CA (US)

(73) Assignee: Synecor LLC, Chapel Hill, NC (US)

( * ) Notice: Subject to any disclaimer, the term of this patent is extended or adjusted under 35 U.S.C. 154(b) by 1380 days.

(21) Appl. No.: 11/702,000

(22) Filed: Feb. 2, 2007

(65) Prior Publication Data

US 2007/0255379 A1    Nov. 1, 2007

Related U.S. Application Data

(63) Continuation-in-part of application No. 11/055,540, filed on Feb. 10, 2005, now abandoned, and a continuation-in-part of application No. 10/862,113, filed on Jun. 4, 2004, now Pat. No. 7,529,589, and a continuation-in-part of application No. 10/454,223, filed on Jun. 4, 2003, now Pat. No. 7,082,336, and a continuation-in-part of application No. 10/453,971, filed on Jun. 4, 2003.

(60) Provisional application No. 60/765,420, filed on Feb. 3, 2006, provisional application No. 60/515,746, filed on Oct. 30, 2003, provisional application No. 60/516,026, filed on Oct. 31, 2003, provisional application No. 60/525,332, filed on Nov. 26, 2003, provisional application No. 60/525,336, filed on Nov. 26, 2003, provisional application No. 60/543,260, filed on Feb. 10, 2004, provisional application No. 60/634,585, filed on Dec. 9, 2004.

(51) Int. Cl.
*A61N 1/18* (2006.01)
*A61N 1/05* (2006.01)
(52) U.S. Cl. ......... 607/120; 607/117; 607/118; 607/119
(58) Field of Classification Search ........... 607/117–120
See application file for complete search history.

(56) References Cited

U.S. PATENT DOCUMENTS

| 3,522,811 A | 8/1970 | Schwartz et al. |
| 3,645,367 A | 2/1972 | Coleman et al. |

(Continued)

FOREIGN PATENT DOCUMENTS

WO    WO 92/16257    10/1992

(Continued)

OTHER PUBLICATIONS

Peters et al, The Evolution Strategy—A Search Strategy Used in Individual Optimization of Electrical Parameters for Therapeutic Carotid Sinus Nerve Stimulation, IEEE Transactions on Biomedical Engineering, vol. 36, No. 7, Jul. 1, 1989.

(Continued)

*Primary Examiner* — Niketa Patel
*Assistant Examiner* — Joseph Stoklosa

(57) ABSTRACT

The present disclosure describes intravascular systems that may be used for a variety of functions. The elements of the disclosed systems include at least one device body implanted within the vasculature. Electrodes on a lead and/or on the device body itself are used to direct electrical energy to neurological targets. These systems may additionally include one or more fluid reservoirs housing drugs or other agents to be delivered to tissue.

12 Claims, 18 Drawing Sheets

U.S. PATENT DOCUMENTS

| | | | |
|---|---|---|---|
| 3,650,277 A | 3/1972 | Sjostrand et al. | |
| 3,835,864 A | 9/1974 | Rasor et al. | |
| 4,573,481 A | 3/1986 | Bullara | |
| 4,649,936 A | 3/1987 | Ungar et al. | |
| 4,881,939 A | 11/1989 | Newman | |
| 5,154,172 A | 10/1992 | Terry, Jr. et al. | |
| 5,170,802 A | 12/1992 | Mehra | |
| 5,179,950 A | 1/1993 | Stanislaw | |
| 5,199,428 A | 4/1993 | Obel et al. | |
| 5,203,326 A | 4/1993 | Collins | |
| 5,224,491 A | 7/1993 | Mehra | |
| 5,269,303 A | 12/1993 | Wernicke et al. | |
| 5,304,206 A | 4/1994 | Baker, Jr. et al. | |
| 5,318,592 A | 6/1994 | Schaldach | |
| 5,330,507 A | 7/1994 | Schwartz | |
| 5,458,631 A * | 10/1995 | Xavier | 607/117 |
| 5,487,760 A | 1/1996 | Villafana | |
| 5,531,779 A | 7/1996 | Dahl et al. | |
| 5,540,734 A * | 7/1996 | Zabara | 607/46 |
| 5,607,463 A | 3/1997 | Schwartz et al. | |
| 5,651,378 A | 7/1997 | Matheny et al. | |
| 5,690,681 A | 11/1997 | Geddes et al. | |
| 5,707,400 A | 1/1998 | Terry, Jr. et al. | |
| 5,755,750 A | 5/1998 | Petruska et al. | |
| 5,913,876 A | 6/1999 | Taylor et al. | |
| 5,928,272 A | 7/1999 | Adkins et al. | |
| 6,073,048 A | 6/2000 | Kieval et al. | |
| 6,104,956 A | 8/2000 | Naritoku et al. | |
| 6,141,588 A | 10/2000 | Cox et al. | |
| 6,161,047 A * | 12/2000 | King et al. | 607/62 |
| 6,178,349 B1 | 1/2001 | Kieval | |
| 6,231,516 B1 | 5/2001 | Keilman et al. | |
| 6,292,695 B1 | 9/2001 | Webster, Jr. et al. | |
| 6,319,241 B1 | 11/2001 | King et al. | |
| 6,341,236 B1 | 1/2002 | Osorio et al. | |
| 6,347,247 B1 | 2/2002 | Dev | |
| 6,375,666 B1 | 4/2002 | Mische | |
| 6,393,325 B1 | 5/2002 | Mann et al. | |
| 6,415,187 B1 | 7/2002 | Kuzma et al. | |
| 6,442,413 B1 | 8/2002 | Silver | |
| 6,445,953 B1 | 9/2002 | Bulkes et al. | |
| 6,449,507 B1 | 9/2002 | Hill et al. | |
| 6,473,644 B1 | 10/2002 | Terry, Jr. et al. | |
| 6,522,926 B1 | 2/2003 | Kieval et al. | |
| 6,542,774 B2 | 4/2003 | Hill et al. | |
| 6,600,954 B2 | 7/2003 | Cohen et al. | |
| 6,616,624 B1 | 9/2003 | Kieval | |
| 6,622,041 B2 | 9/2003 | Terry, Jr. et al. | |
| 6,671,556 B2 | 12/2003 | Osorio et al. | |
| 6,681,136 B2 * | 1/2004 | Schuler et al. | 607/44 |
| 6,684,105 B2 | 1/2004 | Cohen et al. | |
| 6,721,603 B2 | 4/2004 | Zabara et al. | |
| 6,764,498 B2 | 7/2004 | Mische | |
| RE38,654 E | 11/2004 | Hill et al. | |
| 6,845,267 B2 | 1/2005 | Harrison et al. | |
| RE38,705 E | 2/2005 | Hill et al. | |
| 6,850,801 B2 | 2/2005 | Kieval et al. | |
| 6,865,416 B2 | 3/2005 | Dev | |
| 6,907,295 B2 | 6/2005 | Gross et al. | |
| 6,912,419 B2 | 6/2005 | Hill et al. | |
| 6,934,583 B2 | 8/2005 | Weinberg et al. | |
| 6,957,106 B2 | 10/2005 | Schuler et al. | |
| 6,961,618 B2 | 11/2005 | Osorio et al. | |
| 6,978,174 B2 | 12/2005 | Gelfand et al. | |
| 6,985,774 B2 | 1/2006 | Kieval et al. | |
| 7,076,307 B2 | 7/2006 | Boveja | |
| 7,092,753 B2 * | 8/2006 | Darvish et al. | 604/21 |
| 7,149,574 B2 | 12/2006 | Yun et al. | |
| 7,155,279 B2 | 12/2006 | Whitehurst et al. | |
| 7,155,284 B1 | 12/2006 | Whitehurst et al. | |
| 7,158,832 B2 | 1/2007 | Kieval et al. | |
| 7,162,303 B2 | 1/2007 | Levin et al. | |
| 7,167,751 B1 | 1/2007 | Whitehurst et al. | |
| 7,177,702 B2 | 2/2007 | Wallace et al. | |
| 7,184,829 B2 | 2/2007 | Hill et al. | |
| 7,191,012 B2 | 3/2007 | Boveja | |
| 7,203,548 B2 * | 4/2007 | Whitehurst et al. | 607/39 |
| 7,225,019 B2 | 5/2007 | Jahns et al. | |
| 7,231,260 B2 | 6/2007 | Wallace et al. | |
| 7,236,821 B2 * | 6/2007 | Cates et al. | 607/2 |
| 7,269,457 B2 | 9/2007 | Shafer et al. | |
| 7,277,761 B2 | 10/2007 | Shelchuk | |
| 7,283,875 B2 | 10/2007 | Larsson | |
| 7,292,890 B2 | 11/2007 | Whitehurst et al. | |
| 7,295,881 B2 | 11/2007 | Cohen et al. | |
| 7,299,091 B2 | 11/2007 | Barrett et al. | |
| 7,300,449 B2 | 11/2007 | Mische | |
| 7,305,265 B2 | 12/2007 | Fukui | |
| 7,321,793 B2 | 1/2008 | Ben Ezra et al. | |
| 7,336,997 B2 | 2/2008 | Fukui | |
| 7,346,398 B2 | 3/2008 | Gross et al. | |
| 7,363,076 B2 | 4/2008 | Yun et al. | |
| 7,363,082 B2 | 4/2008 | Ransbury et al. | |
| 7,366,571 B2 | 4/2008 | Armstrong | |
| 7,389,149 B2 | 6/2008 | Rossing et al. | |
| 7,395,119 B2 | 7/2008 | Hagen et al. | |
| 2002/0026228 A1 | 2/2002 | Schauerte | |
| 2002/0183791 A1 * | 12/2002 | Denker et al. | 607/5 |
| 2003/0229380 A1 | 12/2003 | Adams et al. | |
| 2004/0010303 A1 | 1/2004 | Bolea et al. | |
| 2004/0019364 A1 | 1/2004 | Kieval et al. | |
| 2004/0024439 A1 * | 2/2004 | Riso | 607/117 |
| 2004/0106954 A1 | 6/2004 | Whitehurst et al. | |
| 2004/0172088 A1 | 9/2004 | Knudson et al. | |
| 2004/0172094 A1 | 9/2004 | Cohen et al. | |
| 2004/0193231 A1 | 9/2004 | David et al. | |
| 2004/0243182 A1 | 12/2004 | Cohen et al. | |
| 2004/0249431 A1 | 12/2004 | Williams et al. | |
| 2004/0254616 A1 | 12/2004 | Rossing et al. | |
| 2005/0043765 A1 | 2/2005 | Williams et al. | |
| 2005/0049655 A1 | 3/2005 | Boveja et al. | |
| 2005/0070974 A1 | 3/2005 | Knudson et al. | |
| 2005/0131467 A1 | 6/2005 | Boveja | |
| 2005/0131486 A1 | 6/2005 | Boveja et al. | |
| 2005/0137646 A1 | 6/2005 | Wallace et al. | |
| 2005/0143779 A1 | 6/2005 | Libbus | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1 | 7/2005 | Libbus et al. | |
| 2005/0154437 A1 | 7/2005 | Williams et al. | |
| 2005/0187586 A1 | 8/2005 | David et al. | |
| 2005/0187589 A1 | 8/2005 | Wallace et al. | |
| 2005/0197675 A1 | 9/2005 | Cohen et al. | |
| 2005/0203599 A1 | 9/2005 | Garabedian et al. | |
| 2005/0203600 A1 | 9/2005 | Wallace et al. | |
| 2005/0216070 A1 | 9/2005 | Boveja et al. | |
| 2005/0228459 A1 | 10/2005 | Levin et al. | |
| 2005/0228471 A1 | 10/2005 | Williams et al. | |
| 2005/0234431 A1 | 10/2005 | Williams et al. | |
| 2005/0251216 A1 | 10/2005 | Hill et al. | |
| 2005/0251238 A1 | 11/2005 | Wallace et al. | |
| 2005/0288730 A1 | 12/2005 | Deem et al. | |
| 2006/0009815 A1 | 1/2006 | Boveja et al. | |
| 2006/0015152 A1 | 1/2006 | Wallace | |
| 2006/0025821 A1 | 2/2006 | Gelfand et al. | |
| 2006/0041277 A1 | 2/2006 | Deem et al. | |
| 2006/0041283 A1 | 2/2006 | Gelfand et al. | |
| 2006/0058854 A1 | 3/2006 | Abrams et al. | |
| 2006/0074453 A1 | 4/2006 | Kieval et al. | |
| 2006/0089678 A1 | 4/2006 | Shalev et al. | |
| 2006/0106429 A1 | 5/2006 | Libbus et al. | |
| 2006/0142801 A1 | 6/2006 | Demarais et al. | |
| 2006/0142802 A1 | 6/2006 | Armstrong | |
| 2006/0195159 A1 | 8/2006 | Bradley et al. | |
| 2006/0212076 A1 | 9/2006 | Demarais et al. | |
| 2006/0212078 A1 | 9/2006 | Demarais et al. | |
| 2006/0224225 A1 | 10/2006 | Ransbury et al. | |
| 2006/0229677 A1 | 10/2006 | Moffitt et al. | |
| 2006/0235474 A1 | 10/2006 | Demarais et al. | |

| | | |
|---|---|---|
| 2006/0247721 A1 | 11/2006 | Maschino et al. |
| 2006/0253161 A1 | 11/2006 | Libbus et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0027492 A1 | 2/2007 | Maschino et al. |
| 2007/0027500 A1 | 2/2007 | Maschino et al. |
| 2007/0038259 A1* | 2/2007 | Kieval et al. .................. 607/44 |
| 2007/0043414 A1 | 2/2007 | Fifer et al. |
| 2007/0066957 A1 | 3/2007 | Demarais et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0135875 A1 | 6/2007 | Demarais et al. |
| 2007/0156201 A1 | 7/2007 | Rossing |
| 2007/0167984 A1* | 7/2007 | Kieval et al. .................. 607/2 |
| 2007/0173899 A1 | 7/2007 | Levin et al. |
| 2007/0203549 A1 | 8/2007 | Demarais et al. |
| 2007/0265687 A1 | 11/2007 | Deem et al. |
| 2008/0004673 A1 | 1/2008 | Rossing et al. |
| 2008/0213331 A1 | 9/2008 | Gelfand et al. |
| 2010/0036451 A1 | 2/2010 | Hoffer et al. |

FOREIGN PATENT DOCUMENTS

| | | |
|---|---|---|
| WO | WO 97/18856 | 5/1997 |
| WO | WO 97/36637 A1 | 10/1997 |
| WO | WO 03/002403 A2 | 10/2003 |
| WO | WO 2004/069331 | 8/2004 |
| WO | WO 2006/031331 A1 | 3/2006 |
| WO | WO 2006/102290 A2 | 9/2006 |
| WO | WO 2006/115877 A1 | 10/2006 |
| WO | WO 2007/013065 A2 | 2/2007 |

OTHER PUBLICATIONS

Cooper et al, Neural Effects on Sinus Rate and Atrioventricular Conduction Produced by Electrical Stimulation from a Transvenous Electrode Catheter in the Canine Right Pulmonary Artery, Circulation Research, vol. 46, No. 1, Jan. 1980.

Goldberger et al, New technique for vagal nerve stimulation, Journal of Neuroscience Methods 91, pp. 109-114, 1999.

Brown et al, Long term bradycardia by electrical pacing: a new method for studying heart rate reduction, Cardiovascular Research, vol. 28, pp. 1774-1779, 1994.

Coleridge et al, Reflex Effects of Stimulating Baroreceptors in the Pulmonary Artery, J. Physiol, 166, pp. 197-210, 1963.

Nabutovsky et al, Lead Design and Initial Application of a New Lead for Long-Term Endovascular Vagal Stimulation, Pace vol. 30, Supplement 1, pp. S215-S218, Jan. 2007.

Li et al, Vagal nerve stimulation markedly improves long-term survival after chronic heart failure in rats, Circulation, 2004.

Bilgutay, Vagal Tuning, A new concept in the treatment of supraventricular arrhythmias, angina pectoris, and heart failure, Journal of Thoracic and Cardiovascular Surg., vol. 56, No. 1, pp. 71-82, Jul. 1968.

Communication from European Patent Office relating to corresponding European Application No. EP 07 763 673.6, attaching PCT Written Opinion for PCT/US2007/002932, corresponding to present application.

PCT Search Report for PCT/US2007/002932, corresponding to present application.

Schwartz et al, Chronic Carotid Sinus Nerve Stimulation in the Treatment of Essential Hypertension, Americal Journal of Surgery, vol. 14, Jul. 1967, pp. 5-15.

Wanner et al, Transvenous phrenic nerve stimulation in anesthetized dogs, Journal of Applied Physiology, vol. 34, No. 4, Apr. 1973, pp. 489, 494.

Watchko et al, Diaphragmatic Pressure in Piglets: Transvenous versus Direct Phrenic Nerve Stimulation, Pediatric Pulmonology, vol. 2, No. 4, Jul.-Aug. 1986, pp. 198-201.

Thompson et al, Bradycardia induced by intravascular versus direct stimulation of the vagus nerve, Ann. Thorac. Surg., 65:637-42, 1998.

* cited by examiner

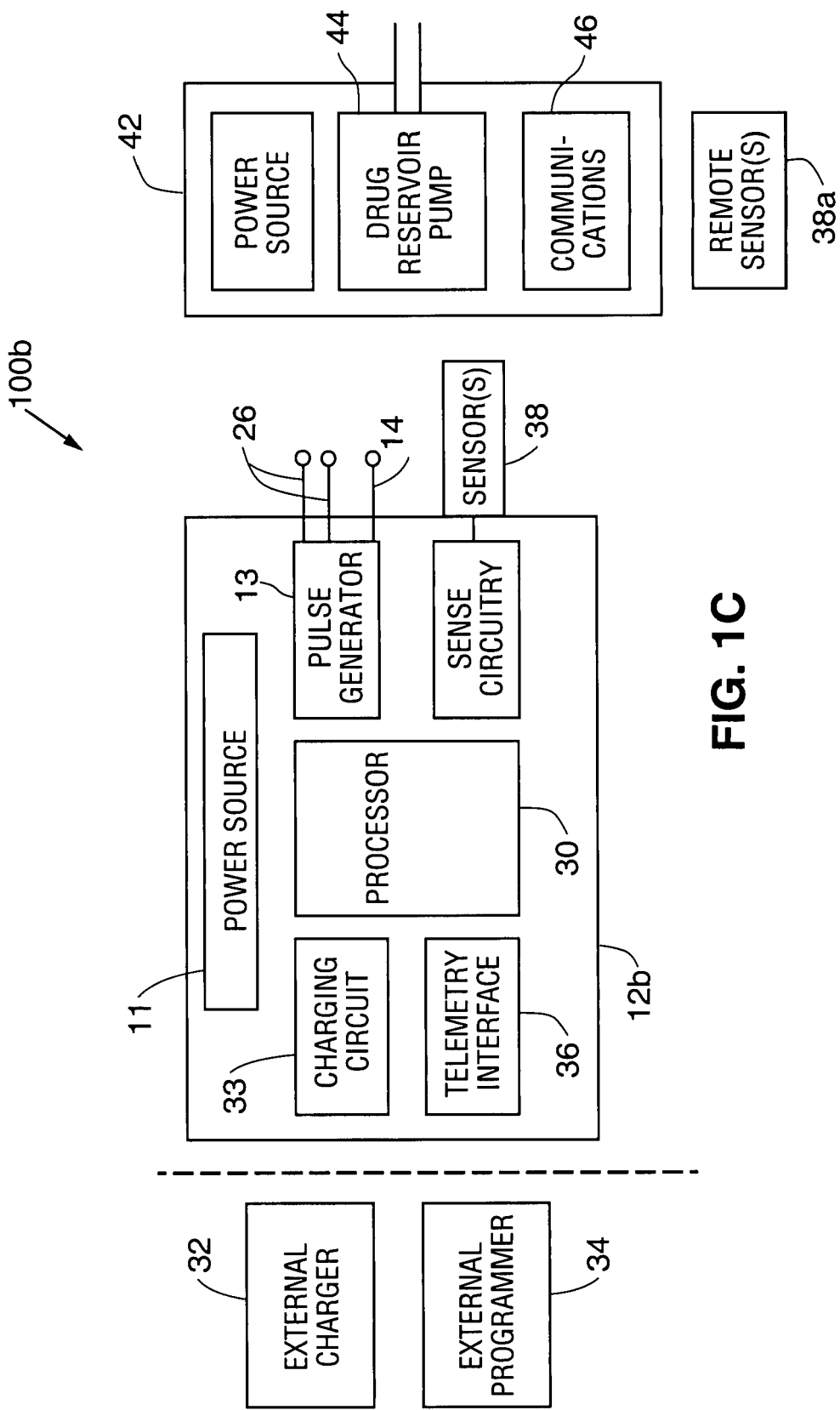

INTRAVASCULAR DEVICE FOR NEUROMODULATION

RELATED APPLICATIONS

This application claims the benefit of U.S. Provisional Application No. 60/765,420, Feb. 3, 2006 and is a Continuation in Part of U.S. application Ser. No. 10/453,971, filed Jun. 4, 2003, and is a Continuation in Part of U.S. application Ser. No. 10/862,113, filed Jun. 4, 2004, now U.S. Pat. No. 7,529,589 which claims the benefit of the following U.S. Provisional Applications: 60/515,746, filed Oct. 30, 2003, 60/516,026, filed Oct. 31, 2003, 60/525,332, filed Nov. 26, 2003, 60/525,336, filed Nov. 26, 2003, and 60/543,260, filed Feb. 10, 2004, and which is also a Continuation in Part of U.S. application Ser. No. 10/454,223, filed Jun. 4, 2003, now U.S. Pat. No. 7,082,336. This application is also a Continuation in Part of U.S. application Ser. No. 11/055,540, filed Feb. 10, 2005 now abandoned. which claims the benefit of 60/543,260, filed Feb. 10, 2004, and claims the benefit 60/634,585, filed Dec. 9, 2004.

This application claims the benefit of U.S. Provisional Application No. 60/765,420, Feb. 3, 2006.

FIELD OF THE INVENTION

The present invention generally relates to implantable devices and systems, and associated methods for delivering therapy to the neurological system.

BACKGROUND OF THE INVENTION

"Neuromodulation" is the therapeutic alteration of activity in the central, peripheral or autonomic nervous systems, electrically and/or pharmacologically, by means of implanted devices. Implantable medical devices are used to deliver neuromodulation therapy to patients to treat a variety of symptoms or conditions. For example, some the implantable medical devices deliver neurostimulation therapy in the form of electrical pulses. For some conditions, electrical stimulation is performed in combination with drug therapy using implantable drug pumps that deliver drugs to the nerves undergoing neurostimulation.

U.S. Publication No. US2005/0043765 ("765 publication") Intravascular Electrophysiological System and Methods (filed Jun. 4, 2004 and commonly owned with the present application), which is incorporated herein by reference, describes intravascular systems that may be used to deliver electrical energy to the heart such as for defibrillation, pacing, and/or cardioversion of the heart.

Such systems include at least one housing containing the necessary pulse generator and associated electronics, circuitry and related components, and they optionally include at least one lead carrying some or all of the electrodes needed to deliver the electrical energy to the body. Some or all of these components are positioned within the vasculature, such as in the superior vena cava ("SVC"), the inferior vena cava ("IVC"), the left or right subclavian vein ("LSV" or "RSV"), coronary sinus and/or within other vessels in the venous or arterial system. For some of the implant components (such as the housing and/or lead), anchoring devices may be needed to retain the implant within the vasculature.

U.S. Publication No. 2005/0234431 ("431 publication"), Intravascular Delivery System for Therapeutic Agents (filed Feb. 10, 2005 and commonly owned with the present application), which is incorporated herein by reference, describes systems for intravascular drug delivery system. Certain ones of the embodiments of the described systems include a reservoir implantable within a blood vessel, an intravascular pump fluidly coupled to the reservoir and an anchor 16 expandable into contact with a wall of the blood vessel to retain the system within the vasculature. Delivery conduits 108 (FIG. 11 of the '431 publication) may extend from the reservoir and are positionable at select locations within the vasculature for target drug delivery to select organs or tissues. Throughout this disclosure, the terms "drugs" and "agent" will be used to refer to any substances to be delivered into the body for any purpose including, but not limited to, prophylactic or therapeutic purposes. In some cases, such substances might also be biologic, such as vector-directed or mediated gene therapy, microspheres containing releasable agents, or stem cells modified to express certain proteins or other therapeutic or diagnostic compounds.

As disclosed in each of the above-referenced applications as well as U.S. Publication No. 2006/0217779 Flexible Hermetic Enclosure for Implantable Medical Devices (filed Mar. 24, 2005 and commonly owned with the present application), which is incorporated herein by reference, these types of implantable devices may be long and narrow for implantation into the vascular, and in some cases can be approximately 10-60 cm in length. Such devices are preferably sufficiently flexible to move through the vasculature yet sufficiently rigid to protect the internal components. Certain embodiments described in the above-referenced patent applications build flexibility into the elongate implants by assembling them using a plurality of segments, with each segment defining interior space for components to be housed within it. Each segment may be separately enclosed by its own enclosure, with several such enclosures coupled together to form the implant. The enclosures are interconnected at articulations formed using silicone rubber filler or mechanical bellows.

It is believed that intravascular devices of the type described in the referenced applications may be suitable for use as neuromodulation devices to delivery electrical and/or pharmaceutical therapy to the nervous system.

BRIEF DESCRIPTION OF THE DRAWINGS

FIGS. 1A-1C are block diagrams showing three exemplary embodiments of neurostimulation systems.

DETAILED DESCRIPTION

Generally speaking, the present disclosure describes intravascular systems that may be used for a variety of functions. In general, the elements of the systems described below include at least one device body and typically, but optionally, at least one lead coupled to the body. The device body (which may include a number of body segments coupled to one another) is ideally positioned fully within the vasculature of the patient. Electrodes on the lead and/or on the device body itself are used to direct monopolar or bipolar electrical energy to neurological tissue or associated structures. These systems may additionally include one or more fluid reservoirs housing drugs or other agents to be delivered to tissue. If drug delivery in combination with electrical therapy is contemplated, the lead(s) may include fluid conduits positioned to direct drugs/agents towards the area of the nervous system that is to be stimulated. Combined delivery of electrical stimulation and drugs/agents might also be used to activate a drug, or to treat a tissue to create an electroporation of a cell to make it more receptive to the administered drug, or to release drugs from drug-containing microspheres having walls that burst or increase in porosity when subjected to electrical stimulation. In other embodiments, neurostimulation is provided using agents (e.g. local application of neurotransmitter, neurotransmitter receptor agonists, neurotransmitter receptor antagonists, or other agents to nervous system target) with or without the use of electrical pulses. Electrical stimulation and/or drug delivery can also be directed to other neurological or non-neurological targets (including organs and/or associated systems) to simulate the release or inhibition of naturally produced agents such as adrenaline or insulin.

Separate fluid delivery leads may also or alternatively be used to direct drugs/agents to an organ (e.g. kidneys, heart) or to other sites remote from the neural tissue undergoing stimulation. One or more anchors/retention devices may facilitate retention of the device body and/or leads or other elements within the vasculature.

Figure 1A:
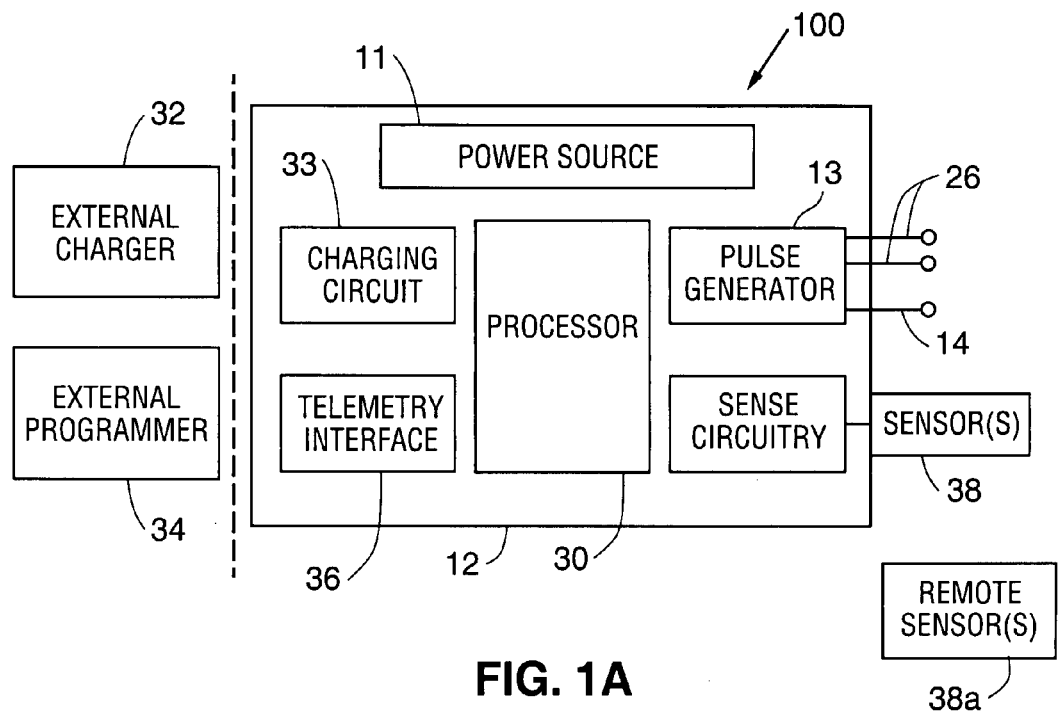
Figure 1B:
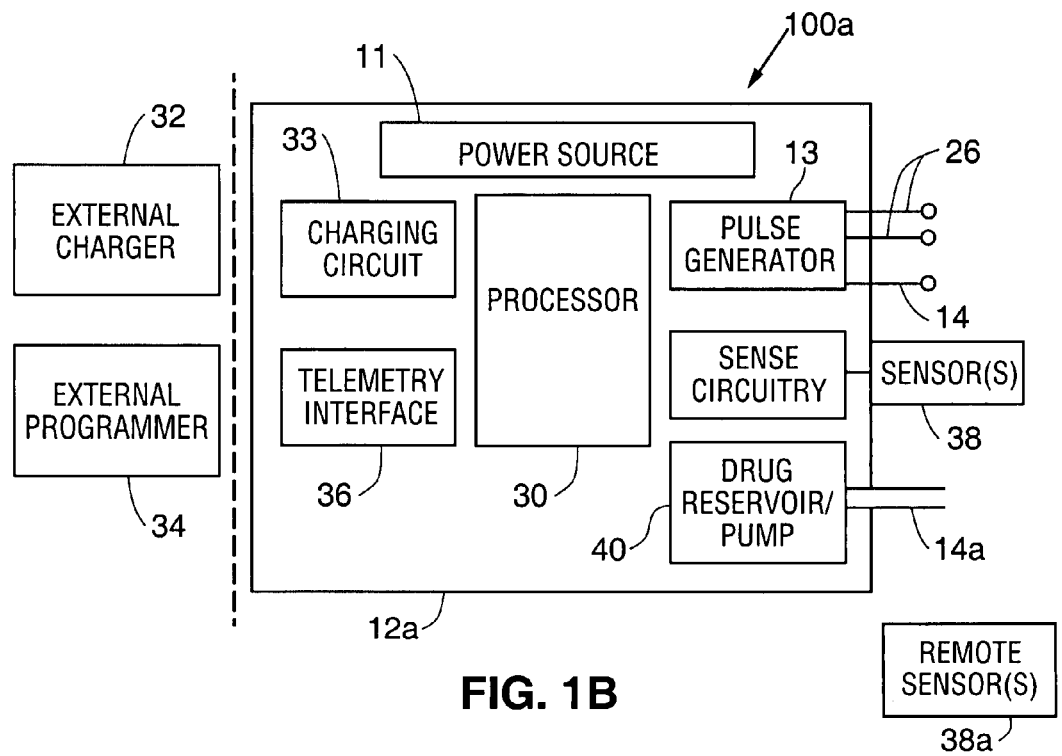

FIGS. 1A through 1C are block diagrams illustrating three exemplary intravascular neurostimulation systems. In the first system 100 shown in FIG. 1A, neurostimulation implant device 12 houses a power source 11 which may include a battery and a power generation circuit to produce operating power stimulation. Device 12 also includes a pulse generator 13 for generating stimulation pulses for transmission to the patient via electrodes 25 on leads 14 or directly on the body of the implantable device 12. A processor 30 may be included for controlling operation of the device 12.

Various stimulation parameters may be used depending upon the target structure and therapeutic application. In general, pulse sequences may use one or all of the following parameters: amplitudes within the range of approximately 1 to 50 mAmp, pulse widths of 1 to 1000 μs, burst rates of 1 to 500 Hz, and programmable duty cycles of 1% to 100%. For some applications, continuous electrical stimulation may be used, or pulse sequences having pulses of different parameters might be employed (e.g. for ventricular rate control in atrial fibrillation, the system might deliver pacing pulses and high-frequency neurostimulation during the atrial refractory period to prevent atrial excitation). The parameters may vary (e.g. ramp up or down) within a pulse sequence, or remain constant. Charge balancing of pulses is appropriate for preventing corrosion/electrolysis of the leads within the tissue. This is generally accomplished using wave forms having biphasic morphology or timing the capacitor recharge cycles such that there is no net imbalance of charge following stimulation.

The functionality of the system 100 may be enhanced using one or a combination of several additional features. For example, the system 100 may include a battery that is rechargeable. An external charger 32 positioned outside the patient inductively couples to a charging circuit 33 within the device 12 to recharge the battery. The external charger 32 includes a charging coil energizable to create an electromagnetic field that in turn induces current in a corresponding coil within the charging circuit 33. The coil may be mounted to a waist pack, wearable skin-contacting/adhering patch, purse, backpack, or wheelchair cushion so that it can be carried by the patient in sufficient proximity to the charging circuit 33. Alternatively, the coil may be positioned within a pad positionable on a patient's mattress, allowing for charging of the battery while the patient rests.

In other embodiments, external charger 32 might be replaced with an external inductive power supply for transcutaneously powering the pulse generator whenever stimulation therapy is to occur, thereby obviating the need for the battery. Energy harvesting techniques may be used by which energy generated by the body may be converted for use in charging the battery and/or operating the system. Piezoelectric elements mounted at various locations in the body might, for example, be used to convert motion of the heart, pulsing blood vessels, limbs, or other structures to electrical energy.

The system 100 may also include an external programmer 34 that communicates with a telemetry interface 36 within the implantable device 12 using radio frequency encoded signals or other telemetric methods. Telemetry systems permitting external devices to communicate with implanted medical devices are known in the art. See, for example, U.S. Pat. Nos. 6,824,561, 5,312,453 and 5,127,404. A user may use the programmer 34 to configure the device 12 (e.g. to set dosing schedules, to set the thresholds above/below which stimulation will be given, to set stimulation parameters), to review the history of therapy given by the implant, to test the implant, to allow the patient to direct release of analgesics for pain control, etc. Where multiple electrodes are employed, the programmer 34 may be used to identify the most optimal electrode pair for stimulating the target structure as discussed in greater detail below.

Sensors 38 can be positioned for detecting certain conditions of the patient and for transmitting signals indicative of the sensed conditions. Signals corresponding to the sensed conditions may be used to trigger the delivery of therapy (see "Control Mechanisms" below) and/or sensor output may be stored within the device for subsequent retrieval using external programmer 34.

Sensors 38 may be located on the device body 12 or the leads 14, or coupled to the device body 12 or leads 14 using cables. For some applications, sensors 38a may be separate implantable or extracorporeal components having communication features allowing them to communicate with the implant 12 via the telemetry interface 36 and/or with external programmer 34.

FIG. 1B shows a second system 10a that differs from the system of FIG. 1A in the incorporation of a drug delivery reservoir and pump features 40 allowing administration of drugs from the reservoir to drug leads 14a (e.g. microtubules) extending from the device. These drug delivery features may be enclosed within the same housing occupied by the other components, or the drug delivery components and neurostimulation components may be divided into two or more separate housings electronically coupled to one another. It should be noted that the FIG. 1A embodiment may be altered to provide only drug delivery, such as for neurostimulation using agents only (e.g. neurotransmitter, neurotransmitter receptor agonists, neurotransmitter receptor antagonists, analgesics), without the use of electrical stimulation.

The system 100b of FIG. 1C is similar to the system of FIG. 1B, but differs in that the neurostimulation features and drug delivery features are contained within physically separate housings. According to this embodiment, the drug reservoir and pump features 40 are enclosed within a container 42 having its own power source 44 as well as communication features 46 for receiving signals wirelessly transmitted by the telemetry interface 36 in the device 12b. With this arrangement operation of the drug delivery pump can be governed wirelessly by the processor housed in the device 12b in a master-slave type configuration. In variations on this embodiment, the arrangement of components might be reversed such that the device 12b includes the slave components remotely controlled by a processor within the container 42. In another variation, both the neurostimulation components of the device 12b and the drug delivery components of the container 42 are wirelessly controlled using a third device implanted within the body (e.g. in the vasculature or in a subcutaneous location) or positioned external to the body. Other systems might employ multiple neurostimulators and/or drug delivery devices independently controlled or controlled using a common master device either directly or wirelessly. In yet another variation using separate drug delivery and neurostimulation implants, one or the other (or both) of the implants may be positionable outside the vasculature.

System Components

Figure 2A:
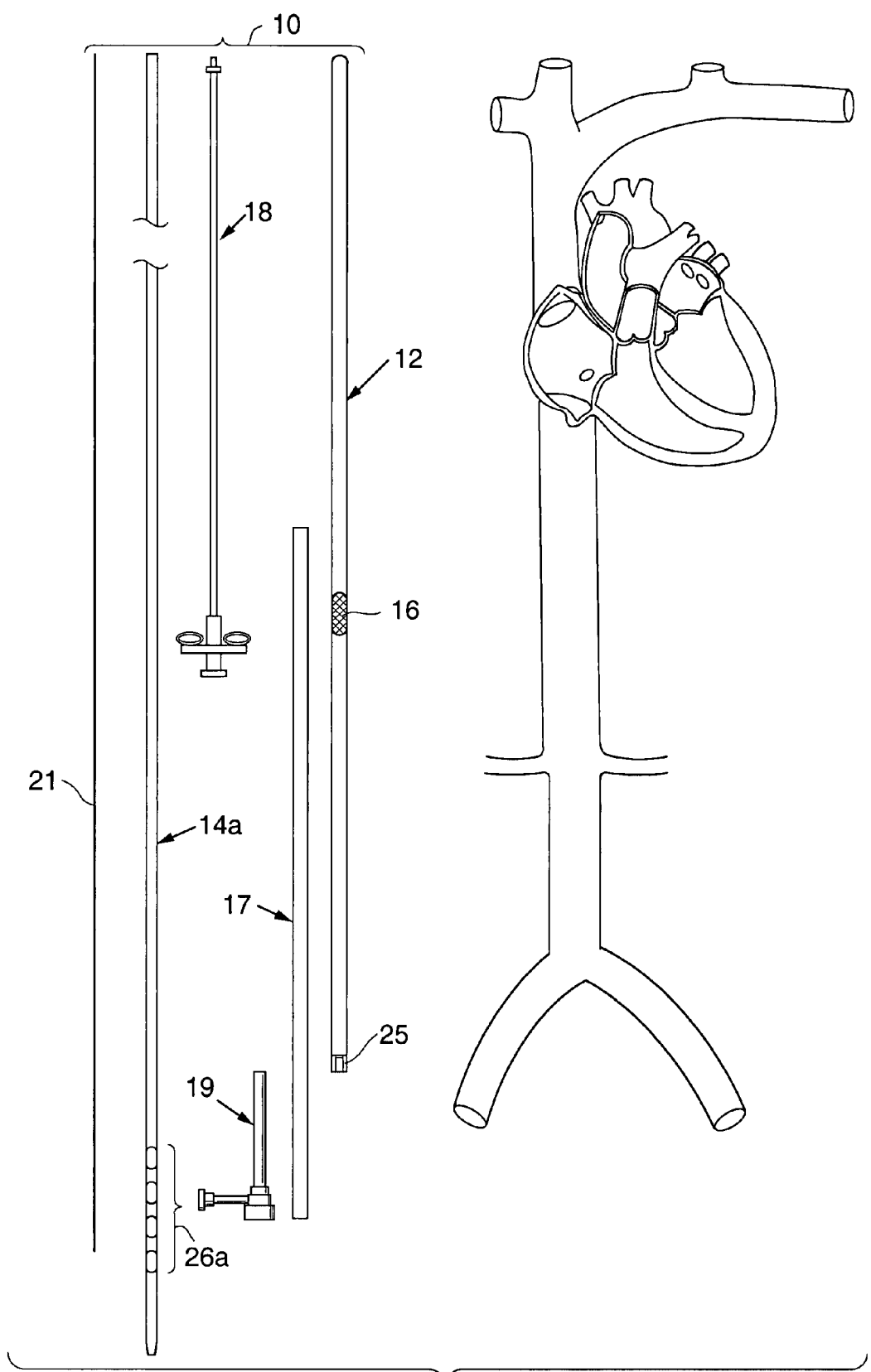
FIGS. 2A and 2B are plan views showing implantable neurostimulation components and associated implant tools.
Figure 2B:
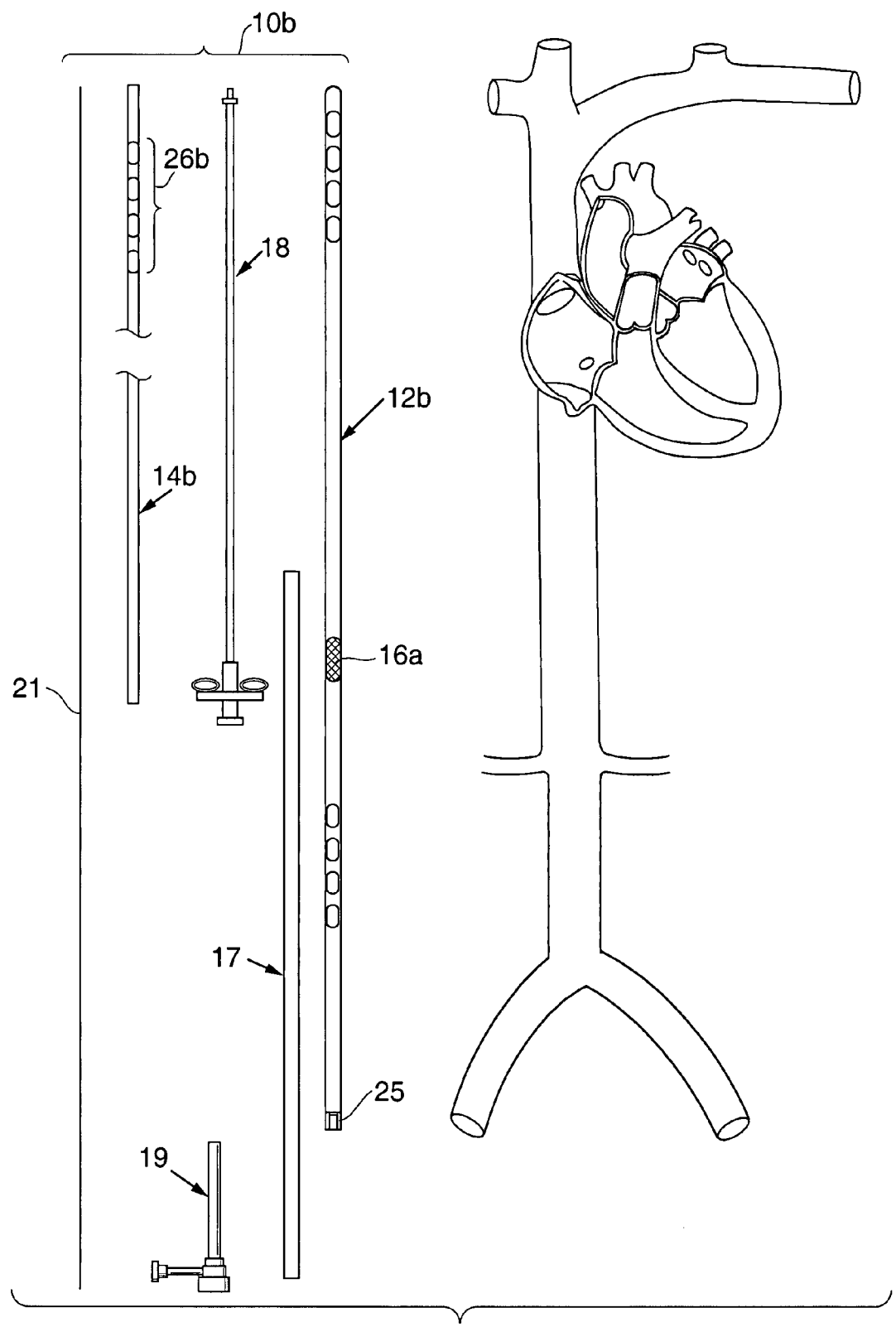
Figure 3:
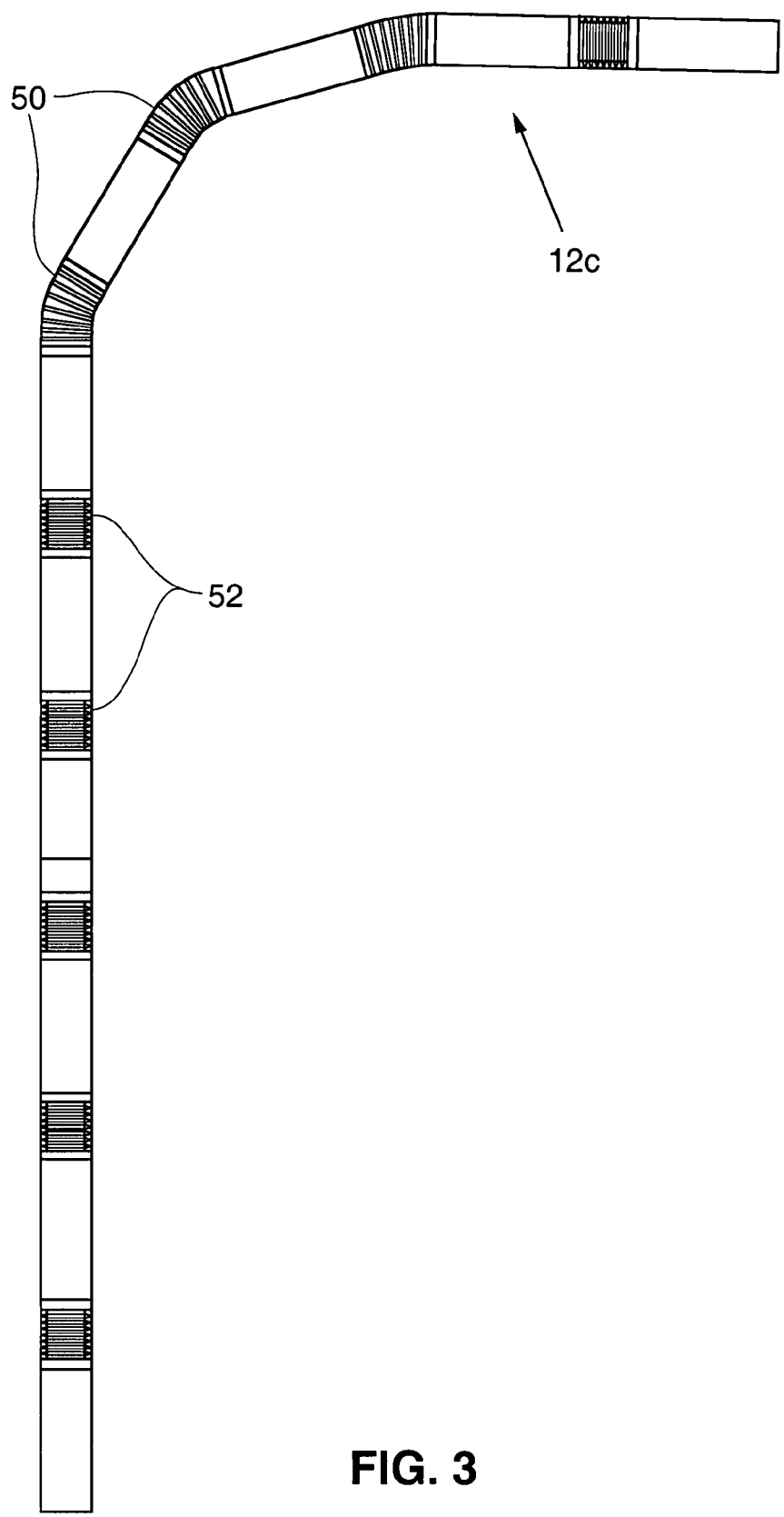
FIG. 3 is a plan view of an implant showing flexible interconnects between portions of the implant.

FIGS. 2A and 2B illustrate exemplary neuromodulation devices and associated components for use in implantation and anchoring of the devices.

The elements of the FIG. 2A system include elongate device body 12, lead 14, retention device 16, sleeve 17, positioning mandrel 18 and introducer sheath 19. It should be understood that certain of these elements may be eliminated, or others added to the system, without departing from the spirit and scope of the invention.

As discussed in connection with FIGS. 1A-1C, device 12 houses components known in the art to be necessary to carry out the system functions. For example, device 12 may include one or more pulse generators, including associated batteries, capacitors, microprocessors, and/or circuitry for generating electrical stimulation pulses and/or drug reservoirs and associated pumps associated with drug delivery. The '431 publication provides examples of features drug reservoirs, pumps or other drug delivery mechanisms, and other features that may be included in a neuromodulation device having drug delivery capabilities. As discussed in greater detail in the section entitled "Control Mechanisms", device 12 may include sensors and detection circuitry for detecting the onset of neurological episodes (e.g. seizures) or other conditions within the body, and/or it may be equipped to directly or wirelessly receive feedback signals from sensors positioned elsewhere inside or outside the body. The specific sensors and other components to be provided in the device will depend upon the application for the device.

The device 12 is proportioned to be passed into the vasculature and to be retained within the patient's vasculature. Suitable sites for the device 12 may include, but are not limited to, the venous system using access through the right or left femoral vein or the subclavian or brachiocephalic veins, or the arterial system using access through one of the femoral arteries. Specific vessels within which the device can be retained include the superior vena cava, inferior vena cava, jugular vein, subclavian vein, axillary vein, and the iliac vein, amongst others.

If the device is to be positioned in an essential blood vessel, it is desirable to minimize obstruction to blood flow presented by the device. In that case, the transverse cross-sectional area of the implant is preferably <50% of that of the vessel. Thus, the housing of device 12 preferably has a streamlined maximum cross sectional diameter which may be in the range of 1-15 mm or less, with a most preferred maximum cross-sectional diameter of 1-8 mm or less. The cross-sectional area of the device in the transverse direction (i.e. transecting the longitudinal axis) should be as small as possible while still accommodating the required components. This area may be within the range of 5-175 mm. Other acceptable ranges of cross-sectional areas are those within the ranges of approximately 79 $mm^2$ or less approximately 40 $mm^2$ or less, or 12.5-40 $mm^2$ The cross-section of the device (transecting the longitudinal axis) may have a circular cross-section, although other cross-sections including crescent, flattened, or elliptical cross-sections may also be used. It is highly desirable to provide the device with a smooth continuous contour so as to avoid voids or recesses that could encourage thrombus formation on the device.

Depending on the components to be included in the device 12, the device may utilize a single- or multiple-compartment housing having a length in the range of 1-100 cm.

A proximal portion of the device includes a connector 25 for receiving the distal end of positioning mandrel 18, which may be used to steer the device 12 (by pushing, pulling and/or torquing) through the patient's vasculature to a target location as described in detail in the above-referenced applications. The connector 25 may take the form of a threaded bore for receiving a threaded screw member at the distal end of the mandrel 18, or it may have any other type of configuration for detachably engaging the distal end of the mandrel. Mandrel 18 can also function as an explant tool used to engage the device 12 and withdraw it from the body.

Mandrel 18 may serve purely mechanical purposes, or it may also be a "smart mandrel" that provides electrical and/or fluid connections. Such connections can be used to couple the device (via an instrument cable) for electrical, electronic, and/or fluid communication between the device and instrumentation located outside the body. This communication may be used for several purposes, including device testing, initiation and/or programming during implantation, and/or recharging of the device battery. If the device is to be used for drug delivery, the mandrel may be used for re-filling a reservoir in the device with drugs/agents that may be deliverable by the device to a patient.

The position of the lead 14 relative to the device is preferably selected to orient the lead in the direction of the vessels (relative to the vessel in which the device body 12 is positioned) that will receive the lead 14. In the FIG. 2A example, lead 14 is attachable to the inferior end of device 12 (the lead 14 may alternatively be integrally connected to the device). Lead 14 includes one or more electrodes 26 configured to pass electrical energy through wall of the surrounding vessel into the targeted neurological structure or directly into the neurological tissue.

Including a number of separate electrodes (e.g. a longitudinal array of electrodes, which may number from 2-16 or more, or a two- or three-dimensional electrode grid such as a 4×4 grid) per lead can provide a number of advantages. For example, where many electrodes are provided, the system can electronically change which of electrodes in the array serves as the anode and which serves as the cathode, such that the effective site of stimulation can be moved without physical repositioning of the lead. The precise location of a neurological target may not always be known. With this capability, the system can sample various electrode pairs to evaluate which combination of electrodes will yield the most optimal response to stimulus. It is contemplated that such electronic manipulation of the electrodes can be done real time and continuously to provide for either isolated point stimulation using closely spaced electrodes or broad tissue capture using more widely separated electrodes. It is also contemplated that the movement of the stimulation site might be useful in managing/reducing damage or sensitization of local tissue to stimulation.

Another advantage to the use of multiple electrodes or electrode pairs is that it allows for selective stimulation by means of using various electrode pairs to interfere with the propagation of electrical impulses in one direction while simultaneously (or sequentially) using separate electrode pairs to induce electrical stimulus propagation in the opposite direction along nerve fibers.

Examples of electrodes that might be used include surface electrodes or tip electrodes. In other embodiments, electrodes that engage the walls of the surrounding vessel might be used. For example, an electrode may be an expandable electrode similar in structure to the anchor 16, or the anchor 16 may be provided with multiple electrodes formed on or mounted to it. This type of embodiment might take the form of a polymeric stent-like grid with an array electrodes, each insulated from the other, throughout the grid structure. This arrangement allows stimulation to be delivered over a greater surface area (e.g. around the inner surface of a vessel wall) and might be particularly useful where the general location of the neurological tissue is known but the precise location is difficult to determine. As another example, the leads may include tip electrodes having penetrating elements that engage the vessel wall. For some applications, leads having electrode-bearing needle tips may be used to allow the electrode(s) to be passed through the vessel wall into the nerve or nerve bundle or to a superficial position from which the lead can be connected surgically to a remote target or a separate remote electrode. The needle tips may include features (e.g. barbs, helices, expandable anchors) that allow them to engage the surrounding neurological tissue. The leads might also be equipped to sense electrical activity of the target structures, such as for detecting the onset of a seizure. In such embodiment, activity sensed by the sensing electrode(s) may be used by the device electronics to trigger delivery of a neurostimulation pulse or one or more pulse sequences.

Additional leads may be provided if desired such that two or more leads may be positioned to stimulate neurological tissue at different locations. Where multiple leads are used, stimulation delivered by each lead may be simultaneous or sequential, or activation of each lead for delivery of therapy may be independent of activation of the other lead(s), with energization of each lead dependent on some sensed condition within the body. The neurostimulation leads may be provided alone or in combination with one or more drug delivery leads (e.g. conduits such as microtubules) positionable to deliver drugs or other agents to organs or other body tissues. Control of drug delivery may be timed to be contemporaneous with, sequential to, or independent of electrical stimulation.

Electrical stimulation leads 14 may be conventional neurostimulation leads, although alternative lead configurations may be desirable if warranted by the desired placement of the device 12 and lead within the body. Leads of the type used for defibrillation and/or pacing may be more suitable for some applications given their suitability for use in the vasculature. The physician will preferably want to select a location for the device 12 within a chosen vessel (e.g. the inferior or superior vena cava or aorta) that will prevent the device from blocking significant peripheral vessels extending from that vessel. An optimal lead will preferably give the physician implanting the device flexibility to position the device at an appropriate location in the chosen vessel without concern that the leads extending from the device will not reach their intended location, but will avoid leaving excess lead length bunched within the vasculature. Thus, for some patients it may be necessary to use a lead that is slightly shorter than defibrillation/pacing leads, or the lead may have a length that is variable/extendable using various techniques such as those described in the '765 publication.

The leads 14 and device 12 may include coatings or coverings made of polymers such as polyurethane. The leads and device may also include non-thrombogenic and/or non-proliferative surfaces or coatings as also described in the referenced applications. For example, the leads and device body may include a coating that is anti-thrombogenic (e.g. perfluorocarbon coatings applied using supercritical carbon dioxide) so as to prevent thrombus formation on the lead. It is also beneficial for the coating to have anti-proliferative properties so as to minimize endothelialization or cellular ingrowth, since minimizing growth into or onto the lead/device will help minimize vascular trauma when the device and/or lead is explanted. The coating may thus also be one which elutes anti-thrombogenic compositions (e.g. heparin sulfate) and/or compositions that inhibit cellular in-growth and/or immunosuppressive agents.

It should also be noted that the lead may be attachable to the device 12 in situ or prior to implantation, or it may be permanently attached to the device, or it may be integral with the device as an elongate extension of the device itself. Thus it should be appreciated that in this disclosure the term "lead" is used to mean an element that includes conductors and electrodes and/or fluid lead conduits and that thus may be positioned somewhat remotely from the circuitry that energizes the electrodes or the reservoir that supplies agents to the fluid conduits. Thus, leads may include elements that are simply extensions or tapers of the device 12 itself (such as the superior portion of the device 12) as well as more conventional leads.

A second embodiment of a device 12 and associated implant components is shown in FIG. 1B and differs from the FIG. 1A embodiment primarily in that its lead 14 is attachable (or integrally attached) to the superior end of device 12. This arrangement might be suitable for use in delivering stimulus to features positioned superiorly relative to the device 12 position within the vasculature.

As further discussed in the '765 application, each of the leads may include a guidewire lumen to aid in implantation of the lead. Referring to FIG. 1, the system may include guidewires 21 for use in implanting the leads. If multi-site stimulation and/or drug delivery is desired, two or more leads may be used. Devices for these applications may include both superior and inferior leads, multiple leads extending from the inferior and/or superior end, and/or leads extending laterally from the device body. Using separate neurostimulation and drug delivery implants as discussed in connection with FIG. 1C gives the user flexibility to deliver different forms of therapy to different regions of the body. For example, a system might include a neurostimulation device be positioned on the venous side of the cardiovascular system and a drug delivery system positioned within the arterial system.

As mentioned, where the device body 12 is particularly long, the body should be sufficiently flexible to move through the vasculature while being sufficiently rigid to protect the internal components. FIG. 2 shows one example of a flexible device body 12c which employs one or more rigid enclosures 50, or "containers," used to contain electronic components to be implanted inside the vasculature of a patient. The containers 50 house components known in the art to be necessary to carry out the system functions. For example, the containers within an implant device can collectively include one or more pulse generators, including associated batteries, capacitors, microprocessors, and/or circuitry for generating electrical pulses for neurostimulation, and or fluid reservoirs and associated pumps for drug delivery. The applications referred above provide additional information of these types of components, as well as suitable arrangements of these components within the device body.

Any appropriate number of the containers 50 can be mechanically connected using interconnecting bellows 52 to form a flexible device. For many devices, this might include a string of at least three containers. The sequence of devices and linking bellows can be repeated as necessary to make a device of an appropriate length. For example, as shown in FIG. 2, a device 12c may have several containers 50 connected using multiple bellows 52 as needed to accommodate the components needed for performance of the device. Additional features of the containers and interconnection mechanisms are disclosed in the above-referenced applications.

The neurostimulation implant device 12 is designed to be retained entirely within the vasculature. Retention within the vasculature can be achieved in one of several ways. For example, if positioned in a non-essential vessel, the device can be retained through frictional contact with the vessel wall. The flow of blood within a vessel can also be relied upon to retain the device in a vessel, preventing the device from migrating upstream while the physical structure of the vessel prevents downstream migration. In other embodiments, anchoring the lead 14 in a blood vessel (i.e. the same or a different blood vessel within which the device 12 is positioned) or outside the vasculature (e.g. through a vessel wall) will serve to retain the device which is coupled to the lead. In other embodiments including those illustrated in FIGS. 5 through 13, an anchor in contact with the device 12 may be used to retain the device within a blood vessel.

Figure 4A:
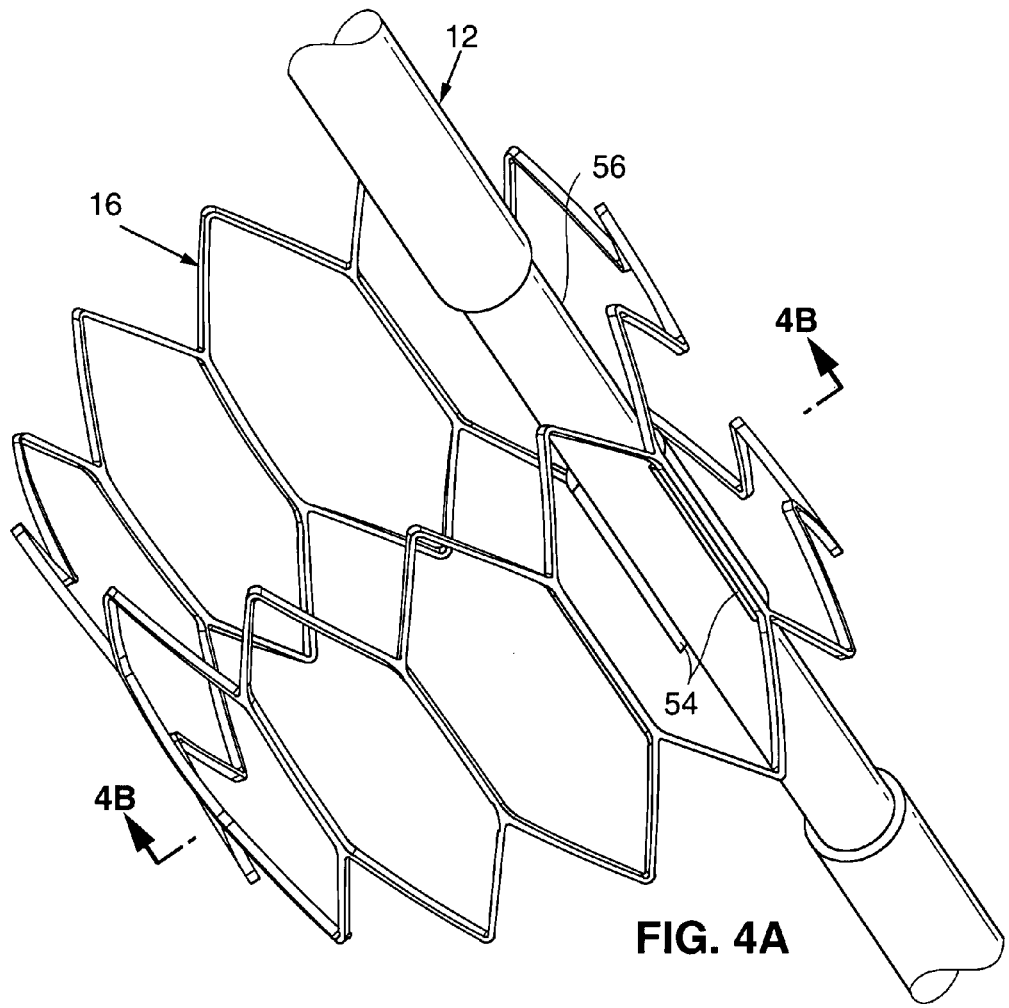
FIG. 4A is a perspective view showing an anchor.

FIGS. 4A though 4D illustrate one example of an anchor 16 of the type that may be used to anchor the device 12 in the vasculature. The anchor 16 is beneficial in that it is implanted integrally with the device, and thus does not require a separate implantation step.

Referring to FIG. 4A, anchor 16 includes structural features that allow the anchor to radially engage a vessel wall. For example, a band, sleeve, mesh or other framework formed of one or more shape memory (e.g. nickel titanium alloy, nitinol, thermally activated shape-memory material, or shape memory polymer) elements or stainless steel, Elgiloy, or MP35N elements may be used. The anchor may include antiproliferative and anti-thrombogenic coatings, although in this embodiment the anchor structure 16 or adapted to promote tissue ingrowth to as to enhance anchor stability within the vessel. The anchor may also have drug delivery capability via a coating matrix impregnated with one or more pharmaceutical agents.

Figure 4B:
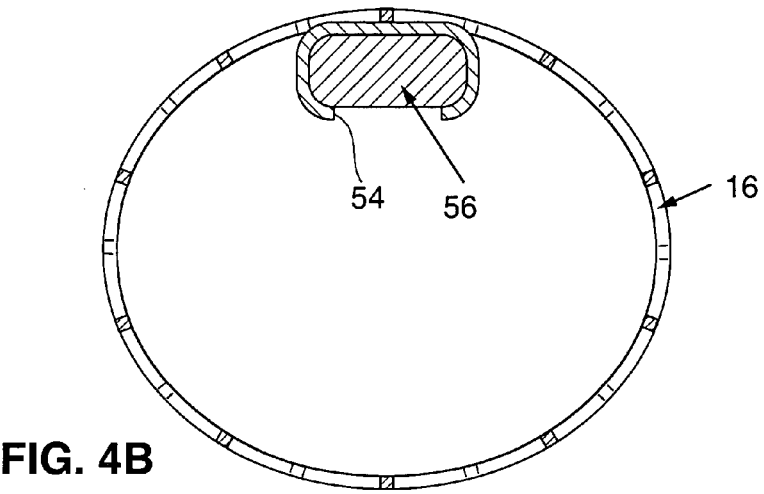
FIG. 4B is a cross-section view taken along the plane designated 4B-4B in FIG. 4A.

FIG. 4B shows one anchor 16 attached to a device 12, although naturally one, two or more such anchors may alternatively be used. In one embodiment, anchor 16 is attached to the implant 12 by a c-shaped collar 54, or other suitable connection. The implant 12 may include a recessed portion 56 that allows the exterior of the anchor to sit flush with the exterior of the implant 12 when the anchor is its compressed position. The recessed portion should have smooth contours in order to discourage thrombus formation on the device.

The anchor 16 and device 12 may be detachably connected to the recessed portion using methods that allow the anchor 16 and the implant 12 to be separated in situ, for permanent or temporary removal of the implant 12. A detachable connection between the anchor 16 and implant 12 may utilize a snap fit between the collar 54 and implant 12. As shown in FIG. 4B, both the collar and the recessed portion 56 of the implant may include an elliptical cross-section. If it becomes necessary to remove the medical implant from the patient's body, the medical implant may be torqued about its longitudinal axis, causing the body of the implant to cam the edges of the collar to a slightly opened position, thereby allowing the implant to be passed between the edges of the collar. Other features of the anchor 16, as well as examples of alternative designs, are discussed in the '765 publication.

Figures 4C, 4D:
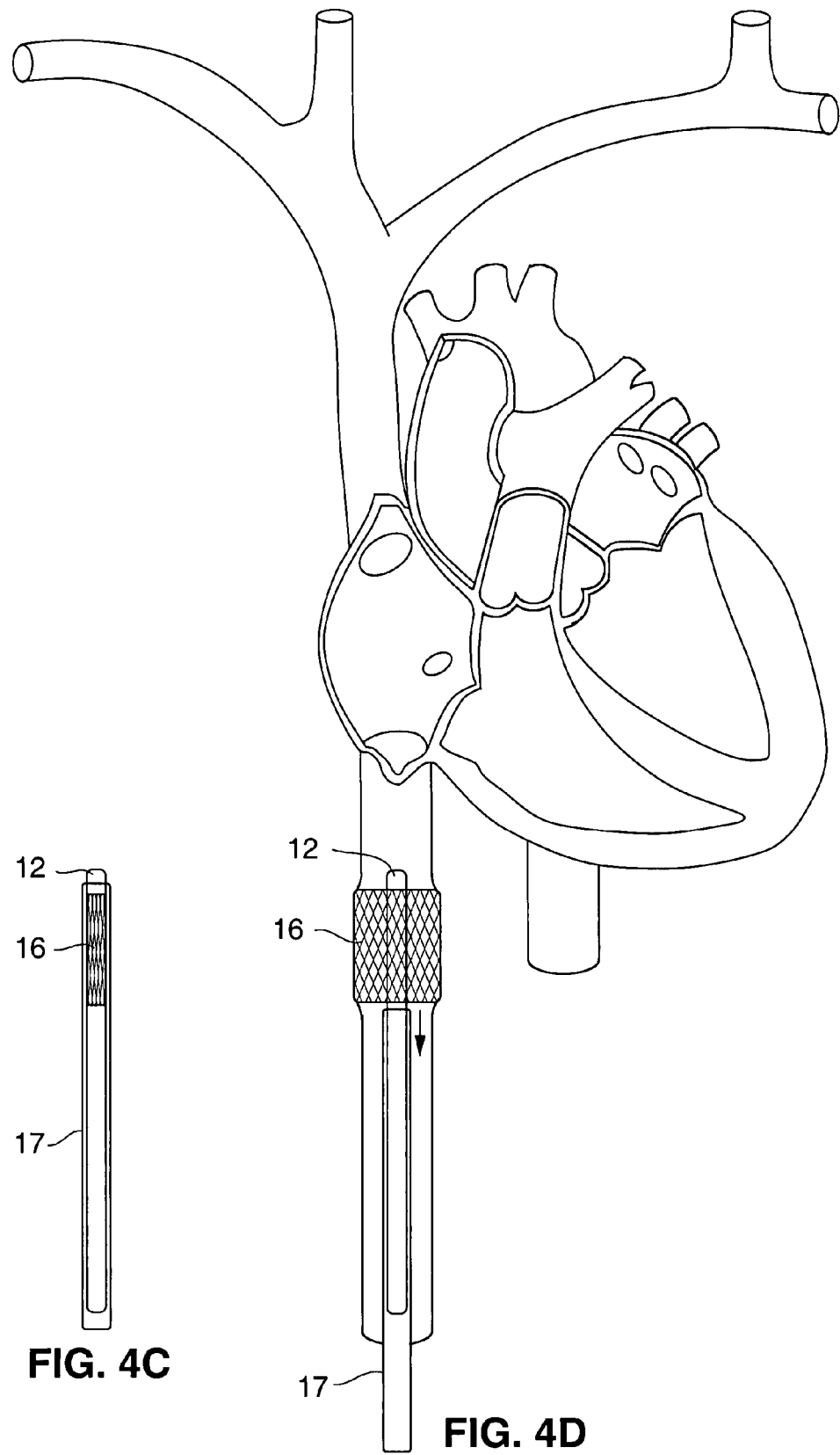
FIG. 4C is a side elevation view of the anchor of FIG. 4A mounted on an implant device and compressed by a sheath.
FIG. 4D schematically illustrates use of the anchor of FIG. 4C to support the implant device within the inferior vena cava.

Referring to FIG. 4C, a retractable sheath 17 may be slidably positioned over the anchor 16 and implant so as to retain the anchor in its compressed position. Retraction of the sheath as indicated in FIG. 4D allows the anchor 16 to expand into contact with the surrounding walls of the vessel, thereby holding the medical implant in the desired location. Once deployed, the anchor 16 is preferably intimate to the vessel wall, which is distended slightly, allowing the vessel lumen to remain approximately continuous despite the presence of the anchor and thus minimizing turbulence or flow obstruction. In other embodiments, the anchor may be deployed prior to the device 12, with the device later attached to the anchor, or it may be deployed after the device 12 with the anchor expandable to sandwich a portion of the device between the anchor and the vessel wall as disclosed in one embodiment of the '431 application.

Control Mechanisms

The device 12 delivers stimulation according to a control mechanism appropriate to the particular application for the device. Exemplary control mechanisms include but are not limited to the following: (a) open loop control, in which asynchronous stimulation is delivered without reference to sensor feedback (e.g. stimulation for pain control); (b) triggered control, in which no stimulation is delivered until a certain condition is detected and then asynchronous stimulation is initiated for a prespecified duration (e.g. stimulation to end an epileptic seizure), and (c) closed loop control, in which one or more feedback variables are actively monitored, and in which stimulator output is modified based on this feedback (e.g. stimulation for control of hypertension by balancing the reduction in heart rate vs elevation of blood pressure). A single system (e.g. any of the systems of FIGS. 1A-1C) can be equipped to use combinations of these control mechanisms for different forms of therapy to be delivered. For example, in a single system, closed loop control might be used for neurostimulation while open loop control is used for drug delivery.

The sensing capabilities of the device will be tailored to the specific application(s) for use. Possible sensing capabilities for inclusion in the device include electrical sensing of physiologic parameters (e.g. heart rate, neurological activity), biochemical sensors for indicators of a given condition, chemical sensing of changes in hormone secretion, ionic balances (e.g. changes in sodium concentrations), or sensing of physical conditions (e.g. blood pressure, physical activity, volume over load, etc). The term "patient conditions" will be broadly used to refer to any type of state or condition that may be detected using a sensor, including but not limited to the sensors and states/conditions expressly identified herein.

The sensors for feedback may be implantable or external, may be permanent or temporary, and may provide their feedback over large variations in sampling rate. They may be configured to transmit signals representing sensed physical/chemical/electrical parameters over the lead, over separate cabling, or through various wireless transmission techniques, or they might be imbedded in the device itself (e.g. a thermistor for core temperature measurements). Some specific types of sensors will be discussed in connection with the embodiments of FIGS. 6-13.

Some applications for the system 10 involve positioning the electrodes at a location in a vessel such that stimulation pulses will conduct from the electrodes through the walls of the vessel to a target nerve located outside the vessel. The system 10 may be provided with detection features allowing determination of the point at which the nerve and the vessel cross one another, so that electrodes nearest the crossing point may be activated for stimulation. Such features might include use of electrodes to monitor electrical pulses from the nerve, or to deliver mild stimulation during implantation so that specific feedback or patient reaction can be detected when the electrode is close to the nerve. For example, in the case of phrenic nerve stimulation, such feedback may take the form of a hiccup triggered in response to stimulation.

Exemplary Methods

For use in performing neuromodulation, a system of the type described above would be positioned within the arterial, venous, or coronary vasculature or in the heart, with leads extending through the vasculature to locations from which electrical stimulus and/or drugs delivered from the leads will deliver a therapeutic benefit to the target neurological structures (such as nerves, the spinal cord, or target regions of brain tissue). For example, for deep brain stimulation, leads might be positioned to deliver therapy to deep brain structures such as the subthalamic nucleus and globus pallidus. In the case of epilepsy, electrodes might be passed through vessels leading to the region of seizure origin as determined by prior testing. Alternatively in the case of epilepsy, brain regions involved in seizures may be affected via stimulation of afferent fibers of the left vagus nerve by electrode(s) placed in cervical or thoracic vasculature.

Where the device is used for electrical or drug stimulation of nerves, stimulation can be targeted to one or more nerves to enhance, augment, inhibit or block signaling of efferent, afferent and/or interneuronal nerve cells, with any combination of these effects being within the scope of this disclosure. Stimulus can be directed to a mixed nerve containing both afferent and efferent nerve cells to produce one effect (e.g. enhance, inhibit or block signaling) on one type of nerve cell (i.e. the afferent or efferent nerve cells), and to produce the same or a different effect (e.g. enhance, inhibit, block, or yield a neutral effect) on the other type of nerve cell. Alternatively, stimulation can be delivered to one or more separate afferent nerves, efferent or interneuronal nerves using the same or different electrodes/fluid conduits to trigger one of these effects (e.g. enhance signaling, inhibit signaling, block signaling, or have a neutral or any combination of the effects).

Figure 5:
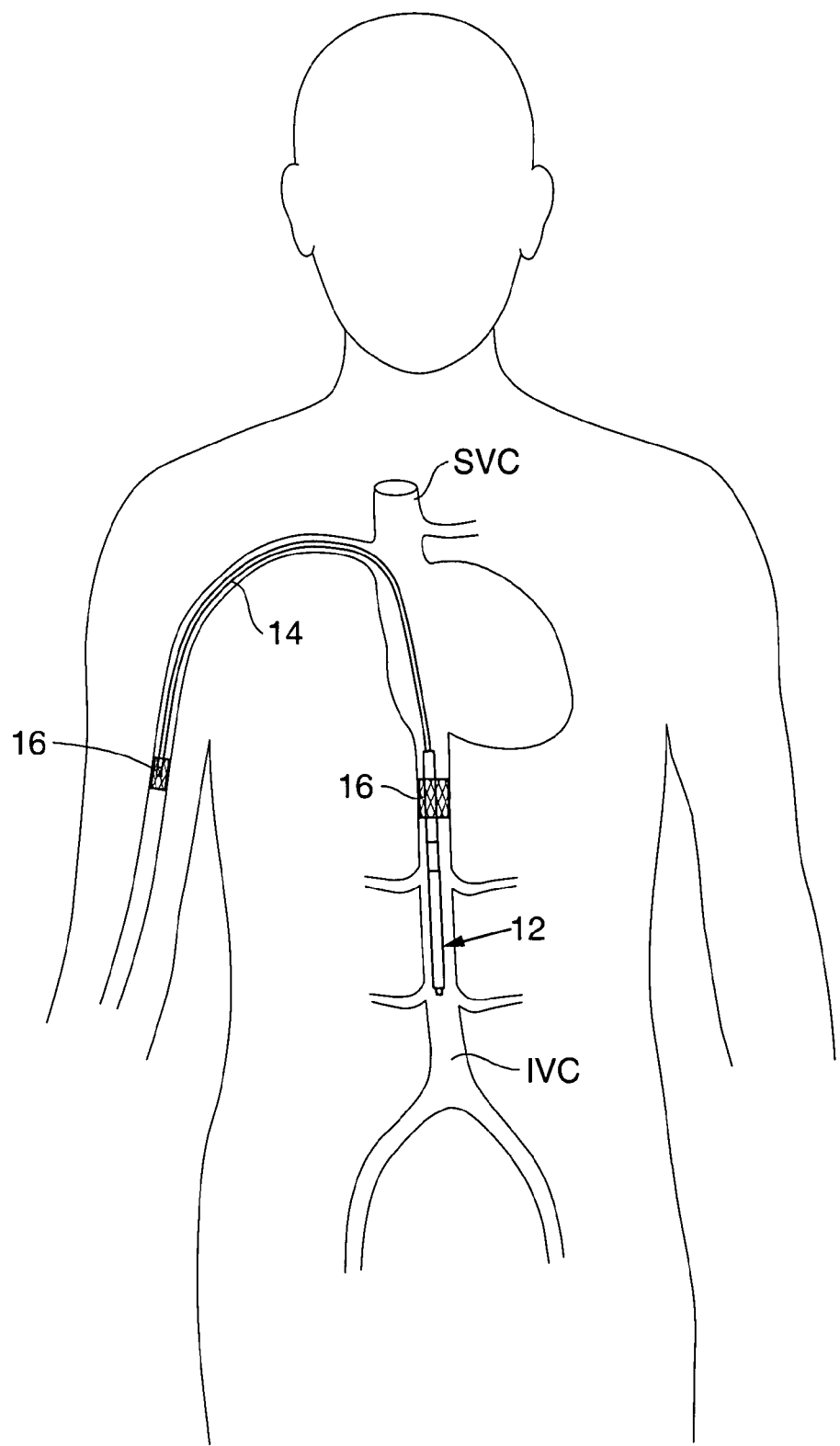
FIGS. 5-13 are schematic illustrations showing the heart and associated vasculature, and illustrating placement of neurostimulation devices within the body.

FIG. 5 illustrates the device 12 positioned in the IVC with the lead 14 extending into the peripheral vasculature (shown schematically) for delivery of therapeutic stimulus to peripheral nerves. In one application, peripheral nerve stimulation might be used to aid movement of a limb experiencing paresis due to peripheral neuropathy. In this application, a sensor is positioned proximal to the site of the nerve damage. When the sensor detects nerve signals indicating that the patient is attempting to move the limb, the electrode is energized to stimulate nerve(s) distal to the nerve damage. The sensed signal may be detected from the damaged nerve at a location proximal to the nerve damage, and the stimulus may be delivered to the damaged nerve at a location distal to the nerve damage, effectively creating a "bridge" across the nerve damage. Lead 14 may similarly function to bridge neural interruptions in a limb that has been reattached. In this example, the lead 14 extends through a blood vessel beyond the point of reattachment so that the electrode is positioned to deliver stimuli to nerve(s) distal to the reattachment. This may require surgical microconnections of the lead 14 to specific areas within the cross-section of the proximal and distal nerve segments. In yet another example, the lead 14 may extend into the prosthetic limb of an amputee. The signals detected by sensor(s) positioned in the body are used to trigger delivery of signals to the prosthesis instructing the prosthesis to move a particular way. In this embodiment, the prosthesis can be configured to select from a preprogrammed menu of movement types based on the nature of the sensed signals.

Various other applications exist for the use of the disclosed neurostimulation systems to bridge neural interruptions at any level within the peripheral or central nervous system.

It should be mentioned with reference to FIG. 5 that an electrical or fluid lead positioned in the peripheral vasculature might also be used to for maintenance of the implant. Thus, a fluid lead might include a port into which agents may be injected using a percutaneous syringe in order to refill a fluid reservoir in the device 12. An electrical lead might include features for transcutaneous recharging of the battery in the device, such as inductive charging, optical charging (e.g. using a light source that transmits light through the skin for impingement onto photovoltaic cell(s) on the lead) or mechanical charging (e.g. transmitting mechanical vibrations through the skin to a piezoelectric element on the lead).

Additional exemplary methods for use of an intravascular system of the type disclosed herein are shown in FIGS. 6 through 13.

Figure 6:
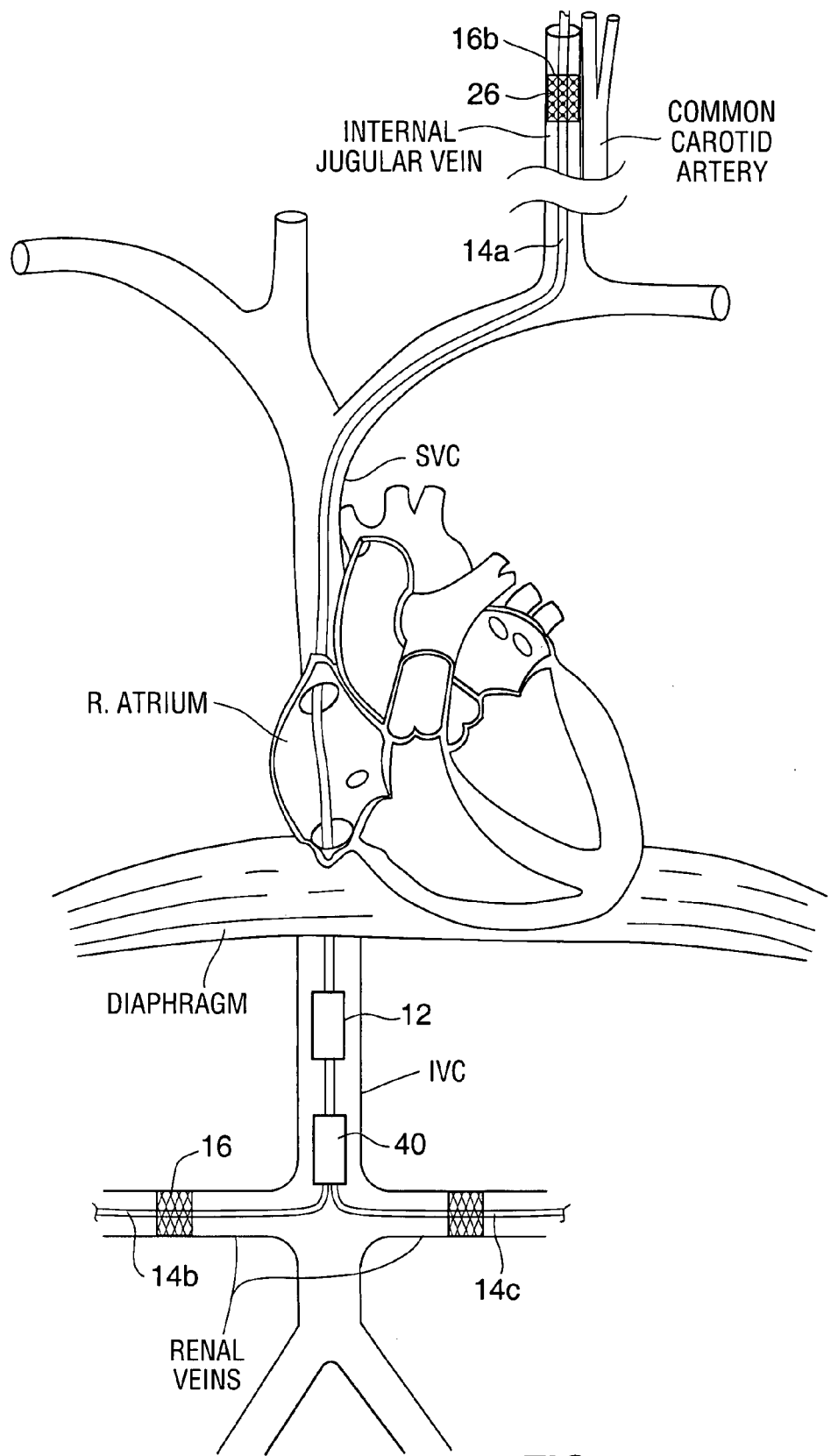
Figure 7:
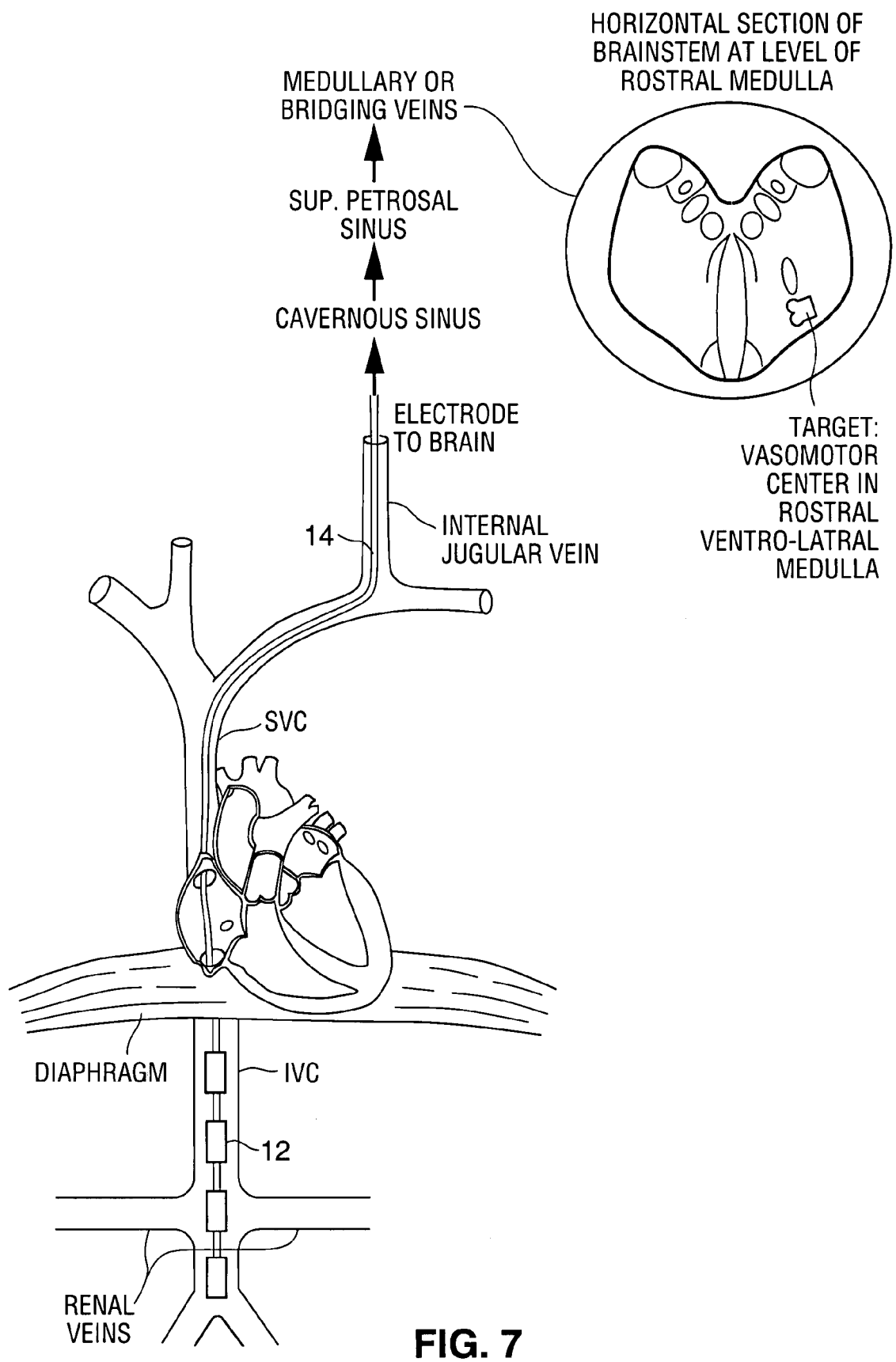

FIGS. 6 and 7 illustrate use of an implantable stimulator for treatment of congestive heart failure ("CHF"). Before the details of the FIGS. 6 and 7 embodiments are given, some background on CHF and the body's response to the effects of CHF will first be described.

In patients with CHF, neurohumoral compensatory mechanisms are activated to maintain circulatory stability in a state of low cardiac output. Neurohumoral activation, particularly activation of the sympathetic nervous and renin-angiotensin-aldosterone systems, works to maintain arterial pressure (via vasoconstriction) and restore cardiac output (by increasing myocardial contractility, heart rate, and intravascular volume). Such compensatory mechanisms are beneficial in the short-term, but can become pathologic over time. Persistent neurohumoral activation contributes significantly to the progressive cardiovascular dysfunction seen in patients with CHF. For example, inappropriate activation of the renin-angiotensin-aldosterone system in CHF promotes salt and water retention in the absence of hypovolemia, increasing preload and increasing myocardial energy requirements on an already-failing heart.

The autonomic nervous system regulates blood pressure by augmenting the tonic rate of sympathetic discharge to smooth muscle in the blood vessel wall. This tonic sympathetic stimulation establishes and maintains vessel tone. Increasing sympathetic discharge causes vasoconstriction, which increases total peripheral resistance (TPR) and therefore increases blood pressure. Decreasing sympathetic discharge causes vasodilation, which decreases TPR and therefore decreases blood pressure. Sympathetic and parasympathetic vasodilator innervation of blood vessels does not play a significant role in determining TPR.

Baseline TPR is established and maintained via tonic sympathetic outflow from the medullary vasomotor center (MVC) in the rostral ventrolateral medulla (VLM). The MVC is the primary site for integration of autonomic regulation of the cardiovascular system. The MVC has reciprocal connections with higher CNS centers (hypothalamus, cerebral cortex) and lower CNS centers (spinal cord nuclei), and additionally receives sensory input from baroreceptors and chemoreceptors.

The baroreceptor reflex pathway triggers rapid compensation for changes in arterial pressure. Baroreceptors (high-pressure mechanoreceptors in the carotid sinus, aortic arch, heart, and lungs) sense blood pressure as "stretch" in the vessel wall. Primary afferent neurons arising from baroreceptors project via the vagal and glossopharyngeal nerves to the nucleus tractus solitarius (NTS). Excitatory output from the NTS projects to the nucleus ambiguus (vagal motor nucleus) and to the caudal VLM, which activates GABAergic interneurons to relay inhibitory signals to the rostral RVM. Efferent projections include 1) inhibitory vagal projections to the heart and 2) sympathetic efferent projections from the RVM to the heart and vasculature via the interomedial column of spinal cord (IML) and sympathetic ganglia. Changes in afferent (baroreceptor) firing frequency are mirrored in vagal efferent firing frequency, and reversed in sympathetic efferent firing frequency. Reflex changes in TPR are governed solely by sympathetic activity. Reflex changes in heart rate are determined by the balance between vagal and sympathetic efferent activity.

Increased arterial pressure causes an increase in baroreceptor firing frequency, which increases inhibitory signaling to the brain stem. This inhibition decreases sympathetic outflow, which causes vasodilation and decreases heart rate, and also increases parasympathetic outflow, which decreases heart rate. The net result of the autonomic response to increased arterial pressure is therefore a rapid, compensatory drop in blood pressure.

Decreased arterial pressure causes a decrease in baroreceptor firing frequency, which decreases inhibitory signaling to the brain stem. This increases sympathetic outflow, which causes vasoconstriction and increasing heart rate, and also decreases parasympathetic outflow, which increases heart rate. These effects combine to increase cardiac output and TPR to prevent further decreases in blood pressure and therefore maintain adequate perfusion to vital organs.

Persistent activation of the sympathetic nervous system begins in the early stages of CHF, and plays a significant role in the natural history of the disease. Such sympathetic "overdrive" attempts to compensate for reduced cardiac output but ultimately accelerates the progression of the underlying ventricular dysfunction. High circulating levels of norepinephrine (NE) induce down-regulation of cardiac β-adrenergic receptors, which impairs cardiac inotropic and chronotropic response. At adrenergic nerve endings, NE release is increased while re-uptake is decreased. α2-receptors, which normally inhibit NE release, are down-regulated. Increased circulating NE levels in heart failure have been implicated in pathologic ventricular remodeling and also in ventricular arrhythmias. Plasma NE levels directly correlate with disease severity and mortality rate in patients with CHF.

In the FIG. 6 embodiment, CHF treatment is achieved using neurostimulation of features of the peripheral nervous system to alter signals sent from baroreceptors of the arterial system to the central nervous system to trigger vasodilation and to thus decrease the heart's workload. In the FIG. 7 embodiment the neurostimulation is directed towards the central nervous system so as to alter signals sent from the central nervous system to prevertebral and para vertebral sympathetic ganglia.

The method illustrated in FIG. 6 treats CHF by stimulating baroreceptors in a manner that causes them to behave as they would when stimulated through expansion of the associated vessel due to an increase in arterial pressure, i.e. so that the baroreceptor produces inhibitory signals that trigger decreases in sympathetic tone, peripheral vascular resistance, and afterload.

Targeted baroreceptors include those in and/or around the heart and large vessels. Tables 1 and 2 lists both barorecepter (mechanoreceptors) and chemoreceptors that might be targeted using electrical and/or chemical stimulation using the disclosed embodiments.

TABLE 1

Mechanoreceptor Locations in Reflex Pathways of Cardiovascular Regulation

Inhibitory baroreceptors
(most vagal-mediated)
Arterial baroreceptors:

adventitia of vessel wall in carotid sinuses (dilatation of vessel just above origin of internal carotid artery)
adventitia of vessel wall of aortic arch
Cardiopulmonary baroreceptors:

atria, especially the right atrium, especially at cavoatrial junctions (SVC, IVC, pulmonary veins) but also diffusely distributed in atrial walls
ventricular walls, left > right
coronary vasculature
pulmonary artery (main pulmonary artery and bifurcation)
Excitatory baroreceptors (sympathetic-mediated)

Diffusely (and somewhat sparsely) distributed throughout atria, ventricles, vena cavae, pulmonary artery, pulmonary veins, pericardium, and aorta (above diaphragm)

TABLE 2

Chemoreceptor Locations in Reflex Pathways of Cardiovascular Regulation

Chemoreceptors proper: sensitive to $\Delta\, P_aO_2$,
also sensitive to $\Delta$ pH or $\Delta\, P_aCO2$ (esp. carotid body)

Carotid body
Aortic Body
Peripheral chemoreceptive cells: vagal-mediated or sympathetic-mediated; opposing pathways triggered in same local region by short-lived chemicals (bradykinin, prostaglandins) produced by hypoxic tissue Juxtapulmonary capillaries, alveolar interstitium (J receptors; pulmonary depressor chemoreflex)
Coronary vasculature (coronary depressor chemoreflex) and left ventricular wall
Right ventricle
Atria
Great veins
Pulmonary artery
Aorta
Central chemoreceptors CNS osmoreceptors (stimulate ADH secretion) located in hypothalamus
Persistent hypoxia → increase sympathetic output from medullary vasomotor center In the illustrated embodiment, electrical stimulation lead 14 extends superiorly from the device 12 and is electrically coupled to electrode anchor 16b, which includes a plurality of stimulating electrodes 26 positioned to contact the vessel walls upon expansion of the anchor 16b. The lead 14 and electrode anchor are positioned such that the associated electrodes are within the internal jugular vein at the level of the carotid bifurcation. This positioning allows the electrodes to stimulate the carotid baroreceptors located in the carotid sinus adjacent to the internal jugular vein. Multiple leads may be positioned at various baroreceptor locations for multi-site stimulation.

In a modification to the FIG. 6 embodiment, stimulation may instead or additionally be directed to afferent neurons that carry signals from the baroreceptors to the central vasomotor center via the glossopharyngeal nerve (which innervates the baroreceptors of the carotid sinus) or the vagus nerve (which innervates the aortic arch baroreceptors), for the purpose of enhancing the inhibitory signaling of the baro-receptors.

Inhibition of the central vasomotor center can also be increased by simulating baroreceptors in the atria or ventricles (e.g. through the use of electrode leads situated in the heart), or by stimulating baroreceptors within the lungs, and/or by positioning the leads such that they will stimulate the afferent vagal neurons that carry inhibitory signals from these baroreceptors to the brain.

According to the method of FIG. 6, stimulation is preferably delivered in response to feedback from one or more sensors positioned on the implant itself, on a separate implant, or located external to the body. Parameters that might be detected include but are not limited to: (a) heart rate and/or Q-T interval determined using an electronic sensor on the device body or lead or external to the body; (b) aortic blood pressure and/or pulmonary artery blood pressure, measured using one of various intravascular pressure sensing techniques known in the art, including capacitive pressure sensors, piezoelectric pressure sensors, temperature differential pressure sensor, flow sensors, etc.; (c) left ventricular chamber dimension determined using echo ultrasound, or measurement of impedance between two closely spaced electrodes within the heart (i.e. using impedance plethysmography determinations); (d) cardiac output using a combination of chamber dimension as determined in (c), plus flow, and heart rates measured using conventional means; (e) chemical sensors for detecting, sodium, calcium, various signaling hormones, $AVO_2$ difference; blood pH (including as an indicator of lactic acid levels in the blood); blood gas levels (including blood $0_2$ and/or blood $CO_2$ levels).

The system might also be responsive to feedback from sensors capable of detecting biochemical markers associated with CHF. Some examples of markers targeted for detection might include:
(a) Triage Cardiac—any combination of a unique set of three biochemical indicators of cardiac muscle necrosis: Mioglobine; CK-MB and Cardiac Troponine I; (b) Tumor Necrosis Factor. Elevated levels of the immune factor tumor necrosis factor (TNFá) may be very strong and accurate predictors of a poor outlook in CHF patients. This immune factor is known to be a potent agent in the inflammatory process; (c) C-Reactive Protein (d) Brain Natriuretic Peptide ("BNP")—a noninvasive, objective marker of Congestive Heart Failure. With regard to BNP, research indicates that The concentration of BNP increases with the severity of CHF (precise correlation with NYHA classification).
BNP concentration has the positive correlation with end-diastolic pressure in left ventricle.
There is a reverse ratio between BNP level and the function of left ventricle after heart infarction.
The increase of BNP level is associated with increasing of Pulmonary Artery Wedge Pressure (precise correlation), deterioration of LV diastolic and systolic functions, LV Hypertrophy and Heart Infarction.

By using the same electrode location as shown in FIG. 6, the carotid baroreceptor may instead be stimulated in a manner that afferent signaling from the baroreceptor indicates increased stretch of the vessel causing the body's feedback control system to believe there is a volume overload condition and thus triggering the efferent signaling to trigger increased natural diuresis. In this example, electrical stimulation patterns would be chosen to achieve the desired effect while at the same time selectively blocking the downstream vasodilation effects. The embodiment shown in FIG. 6 includes drug delivery leads 14b, 14c for delivering suitable agents into the blood within the vasculature and/or the heart. For example, the system may be used to deliver agents used to treat symptoms of congestive heart failure (CHF), including cardiorenal syndrome. Such agents may include agents within the classes of positive inotropes, diuretics, vasodilators, and cytokine effectors. Specific agents include: Dobutamine, Atrial Natriuretic Peptide, Digoxin, Enoximone, Nesiritide, Tezosentan, Bumetanide, Hydralazine, Alprostadil, Carvedilol, Enalaprilat, Ambrisentan, and Levosimendan (sold by Abbott Laboratories under the trade name Simdax). The leads 14b, 14c are coupled to a drug reservoir/pump 40.

In the FIG. 6 arrangement, the leads are positionable to deliver drugs to the kidneys, however, the leads may alternatively be positioned elsewhere in the cardiovascular system, including within the heart. In another embodiment, a two-device configuration like that of FIG. 1C may be used so that electrodes can be positioned in the internal jugular as shown in FIG. 6 as shown, while a separate drug delivery device can be positioned in the arterial system. This allows drug delivery leads 14b, 14c to be anchored in the renal arteries, allowing blood flood to propel drugs from the leads to the kidneys.

In the FIG. 7 embodiment, the neurostimulation device is used to stimulate the central nervous system in order to augment autonomic control of peripheral vascular resistance. The benefits achieved using this embodiment are suitable for treatment of congestive heart failure, as well as hypertension (essential and secondary), diabetes mellitus, and other conditions.

Stimulation may be targeted to one or more of a variety of neurological targets in the brain. In one example shown in FIG. 7, stimulating electrodes are positioned in the brain to deliver electrical stimulus that will inhibit the vasomotor center in the rostral ventro-lateral medulla ("RVLM"). The vasomotor center in the RVLM can be inhibited by low-level electrical stimulation to, for example, inhibitory fibers to the nucleus tractus solitarius, and/or stimulation of GABAergic interneurons projecting to the RVLM. For example, an electrode lead can be passed through the subclavian vein and the jugular vein, and then guided to, for example, a superficial cranial vein. Afterwards, the surgeon palpates the skin to find the lead, forms a small incision to gain access to the lead, threads the lead through a treephine hole drilled into the skull, and advances the lead towards the target area within the brain. In some cases the target area may be determined prior to device implantation using direct electrical stimulation of the brain.

Alternatively, the electrical energy may be conducted transvenously through the vessel walls towards the neurological target without penetration of the vessel wall. Access to the neurological target for direct or transvenous stimulation can be gained via veins of the posterior fossa, the petrosal sinus and petrosal veins, the vein of the middle cerebellar peduncle, the lateral medullary and other medullary veins, the retro-olivary vein, regional bridging veins, as well as through other vessels.

In an alternative embodiment, rather than stimulating the vasomotor center, stimulation may be used to inhibit efferent neurons from the vasomotor center. In this example, stimulation energy can be delivered to any point along the pathway between (and including) the vasomotor center and the prevertebral and paravertebral sympathetic ganglia.

FIGS. 8A through 11 illustrate methods for using an intravascular stimulation device for treatment of sleep apnea. The systems used in carrying out these methods preferably deliver stimulation upon receipt of feedback indicative of a cessation in breathing. Various parameters can be sensed for this purpose, including but not limited to: (a) breathing movements using an accelerometer to detect chest movement or a strain gauge to detect chest expansion; (b) changes in lung volume using impedance plethysmography to measure transthoracic impedance changes; (c) changes in breathing efficiency using an intravascular chemical sensor for detecting blood CO2 or O2 concentrations; (d) sleep state using EEG electrodes positioned on the scalp or within the brain; (e) facial movements, especially rapid eye movement, using an accelerometer; (f) snoring using acoustic detection methods; (g) muscle tone of specific throat structures using electrodes; (g) changes in airway flow rates and pressures to monitor airway patency.

Figure 8A:
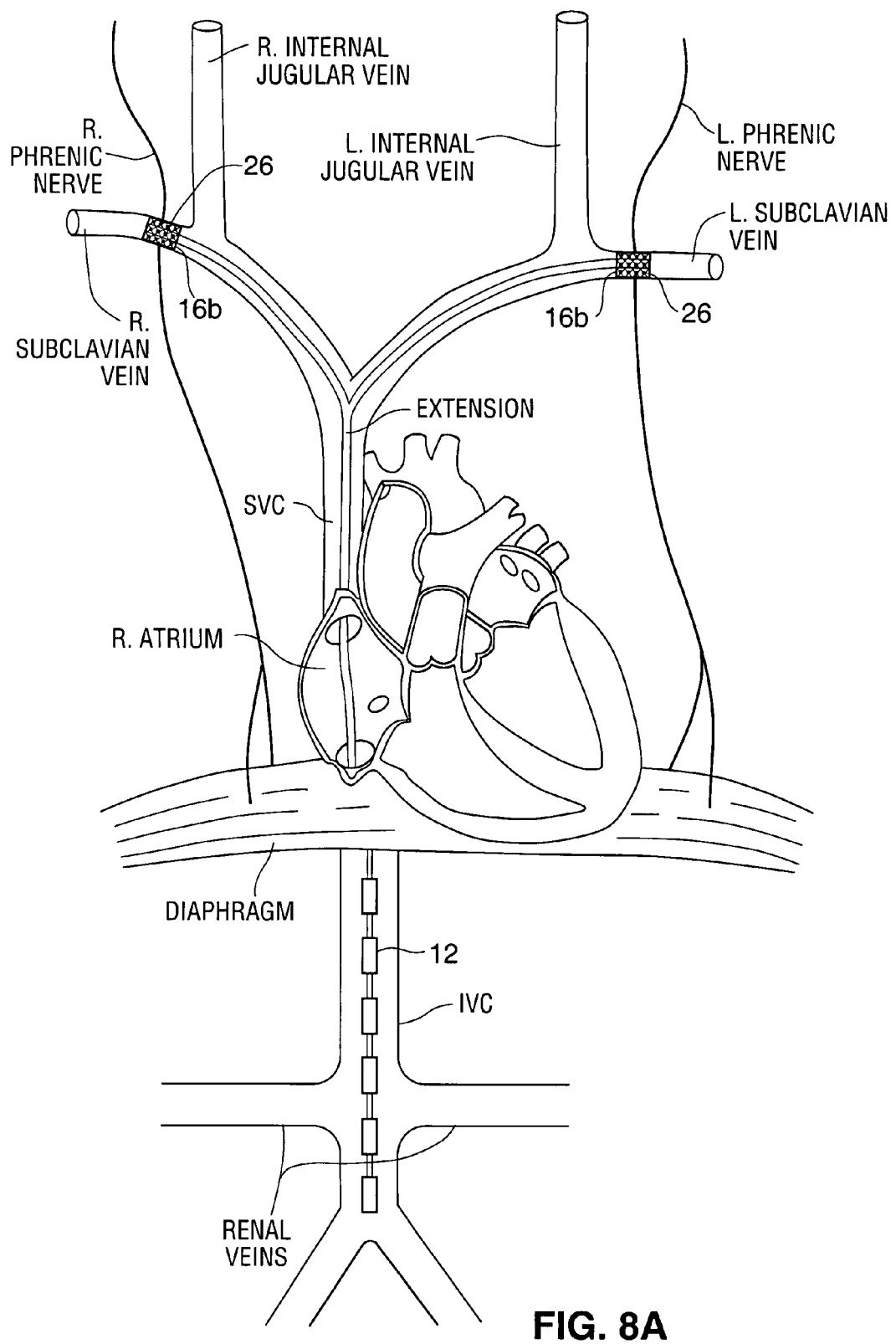
Figure 8B:
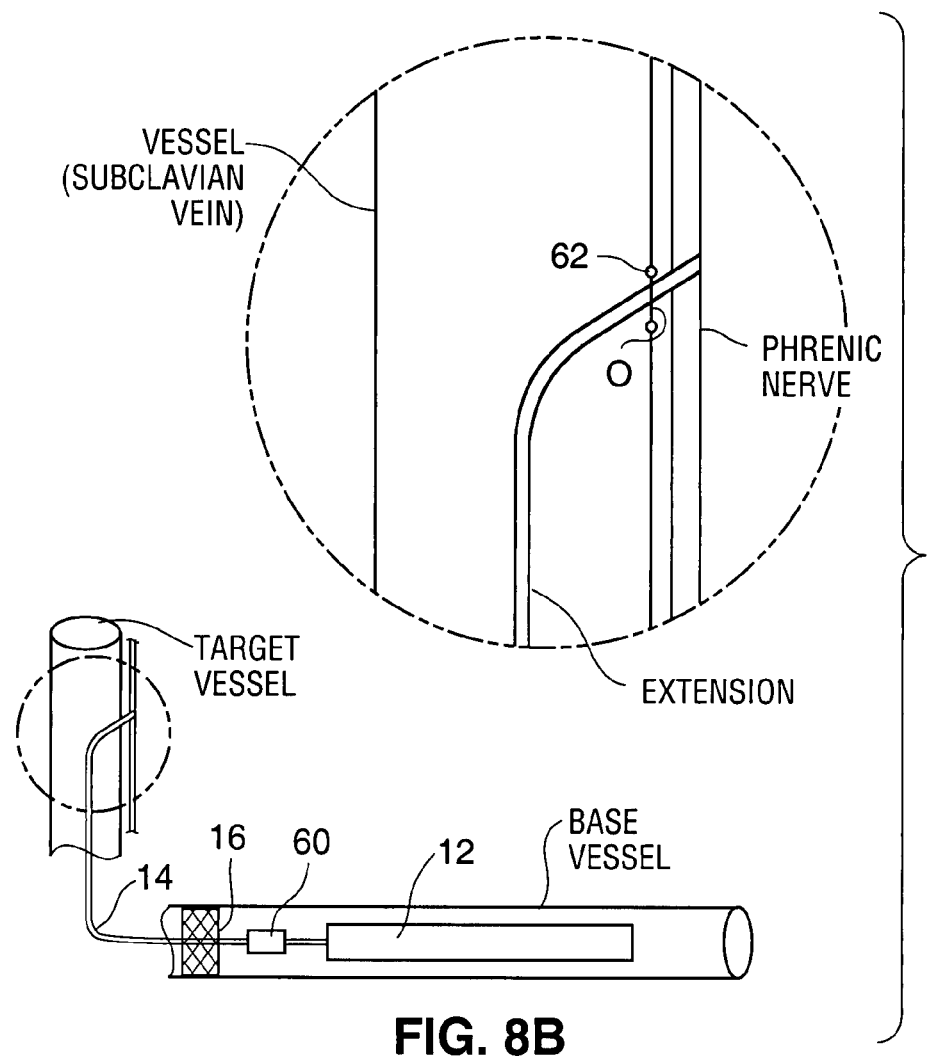

The FIG. 8A embodiment uses phrenic nerve stimulation as a means for treating sleep apnea. For example, in response to detection of a threshold CO2 level by a CO2 sensor 60 positioned on the device 12 or lead 14, one or more stimulating pulses are delivered to the phrenic nerve, causing contraction of the diaphragm to expand the lungs and to thus draw air into the lungs. Similar device positioning might also be used for diaphragmatic pacing to facilitate breathing in patients having neurological injuries or disorders, such as motor neuron disease and spinal cord injury, among others. Devices for diaphragmatic pacing might include features allowing for rate adaptive breathing rate modulation, allowing pacing to be responsive to feedback from one or more sensors indicating various metabolic needs. Suitable sensors include, for example, accelerometers for detecting patient motion, heart rate monitors, and $pCO_2$ and $pO_2$ sensors.

In the illustrated embodiment, electrodes are anchored in the left and right subclavian veins, near the phrenic nerves. According to one electrode positioning method shown in FIG. 8B, electrodes may be positioned directly in contact with the phrenic nerve by extending an electrode lead 14 through an opening O formed in a wall of a blood vessel, preferably at a location near the phrenic nerve. A vascular sealing member or substance 62 may be used to close the opening O in the region surrounding the lead to minimize bleeding. The lead is positioned in contact with the phrenic nerve, or embedded within the nerve tissue, such that by energizing the electrode the nerve may be directly stimulated.

Figure 8C:
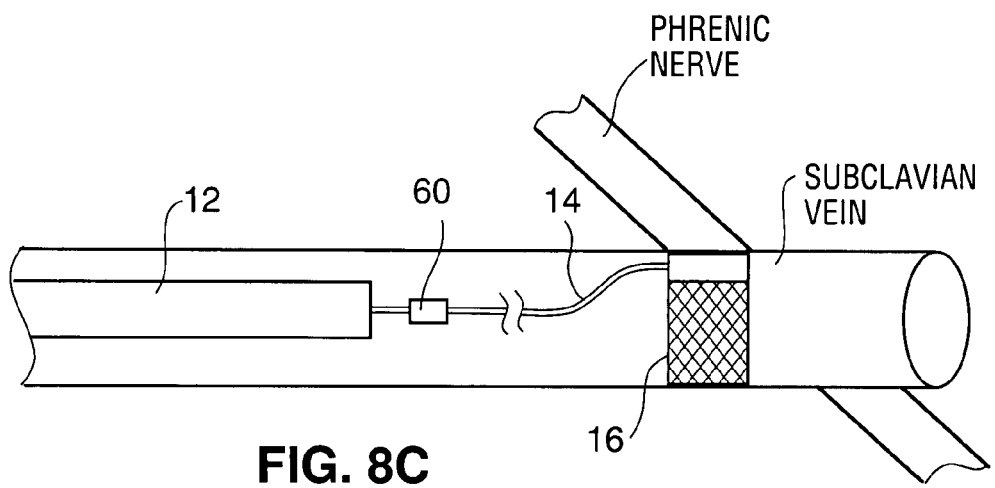

Alternatively, as shown in FIG. 8C, the lead may be positioned within an intact vessel (e.g. a subclavian vein) at a point at which the vessel crosses the phrenic nerve, thus allowing conduction of the electrical stimuli from the electrode through the vessel to the phrenic nerve.

Figure 9:
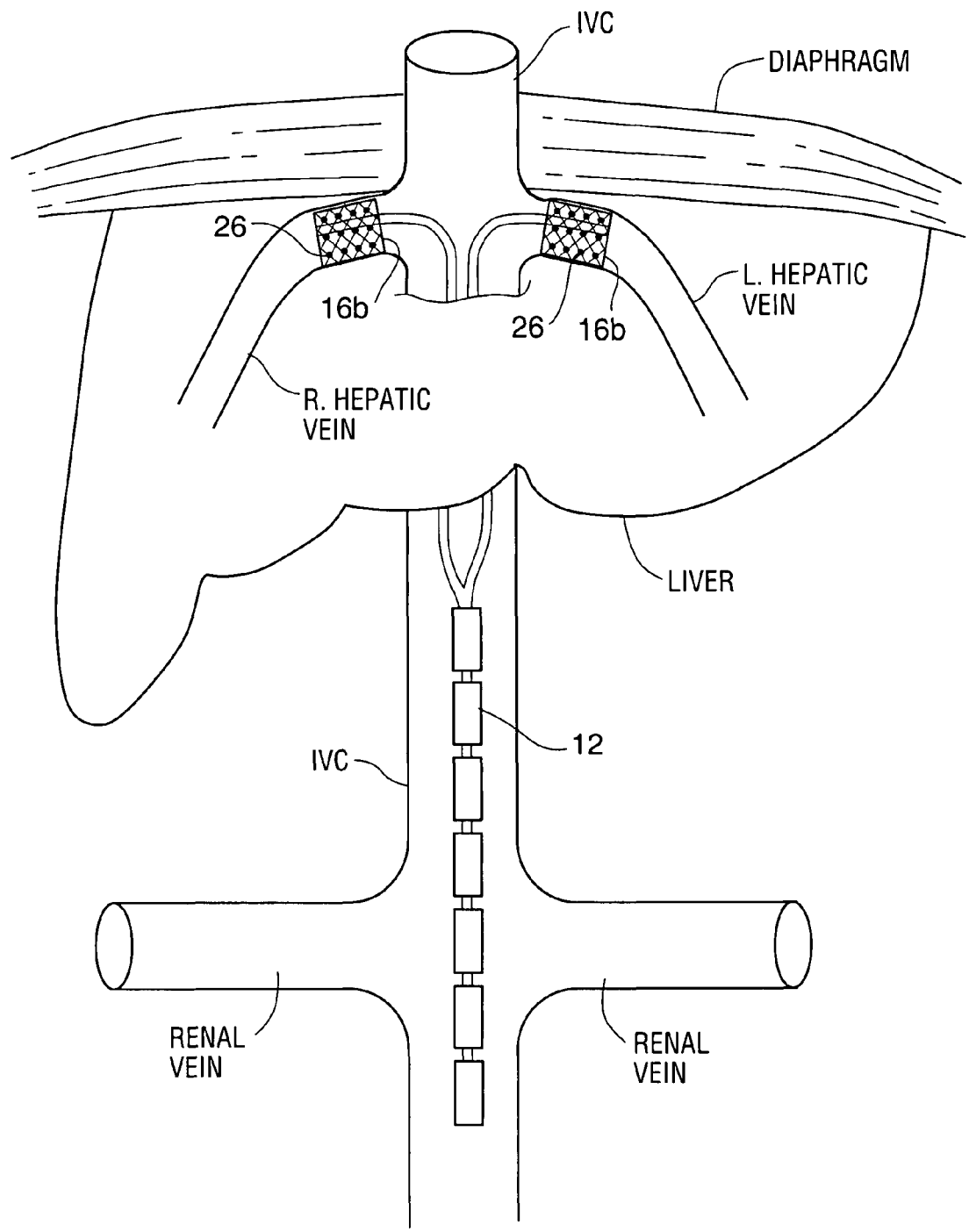

FIG. 9 shows an alternative electrode arrangement suitable for treating sleep apnea. According to this embodiment, electrodes are positioned such that stimulation energy passes transvenously through the walls of blood vessels that are in electrical contact with the diaphragm, thus stimulating the diaphragm. Electrodes may be positioned in the right and left hepatic veins as shown, or in any other sites including but not limited to the inferior vena cava. As with the FIG. 8A embodiment, this embodiment is also suitable as a diaphragmatic pacer to facilitate breathing in patients having motor neuron disease, spinal cord injury, or other diseases/conditions.

Figure 10:
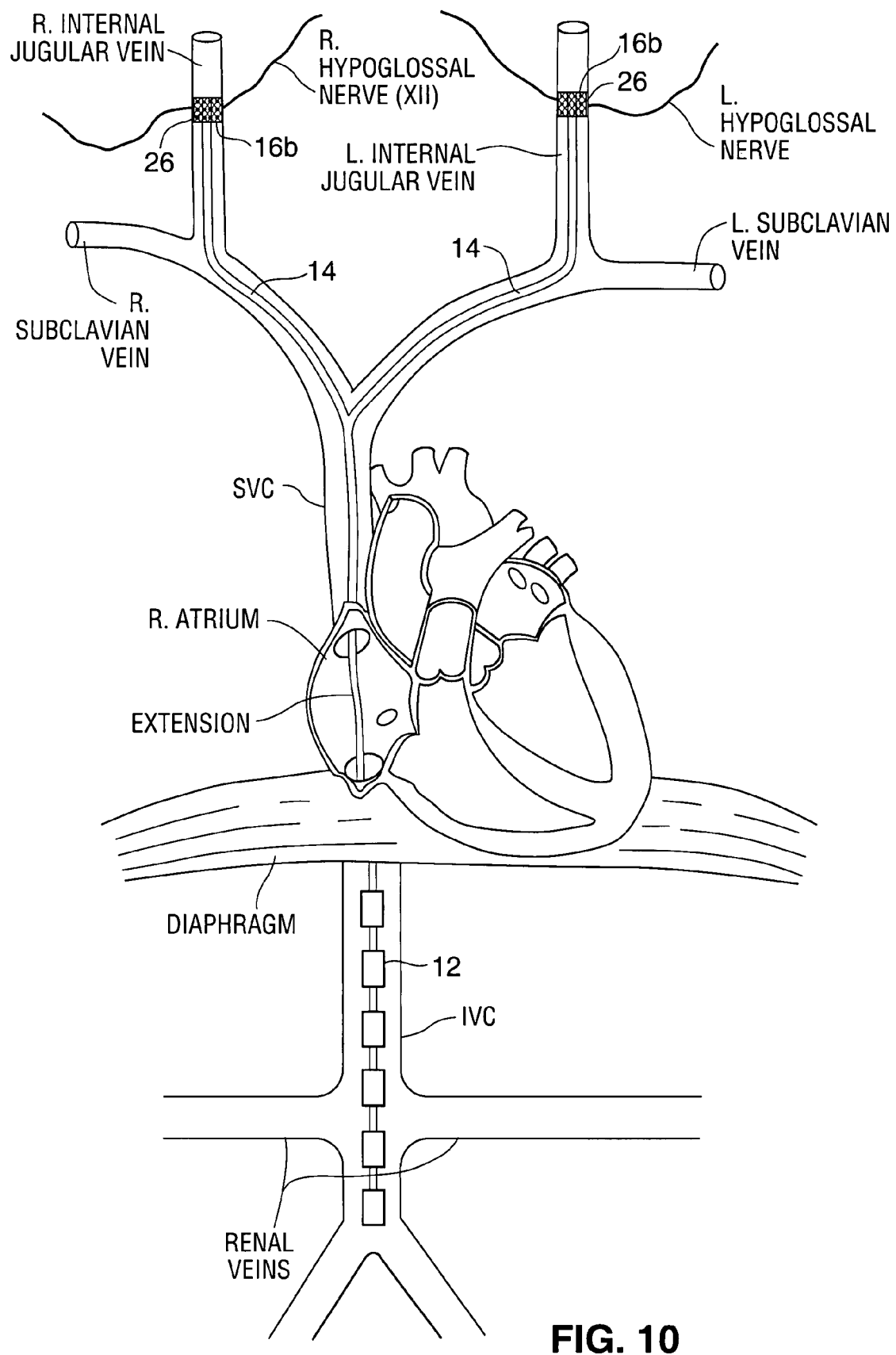

In the FIG. 10 embodiment, electrical stimulation is delivered to the hypoglossal nerve, which innervates the muscles of the tongue. This embodiment may be useful for treating obstructive sleep apnea in a patient whose tongue relaxes during sleep to a point at which the tongue causes an obstruction of the airways. Stimulating the hypoglossal nerve can increase the tone of the muscles of the tongue, thus opening the airways.

In one exemplary electrode position shown in FIG. 10, energy is conducted to the hypoglossal nerve using electrodes anchored in the left and right internal jugular veins, near the points where those veins cross the left and right hypoglossal nerves. If the oropharyngeal muscles are instrumental in obstructing the airway during sleep, the electrodes may be positioned to stimulate the oropharyngeal muscles or the nerves that innervate them, so as to contract those muscles away from the airway.

Figure 11A:
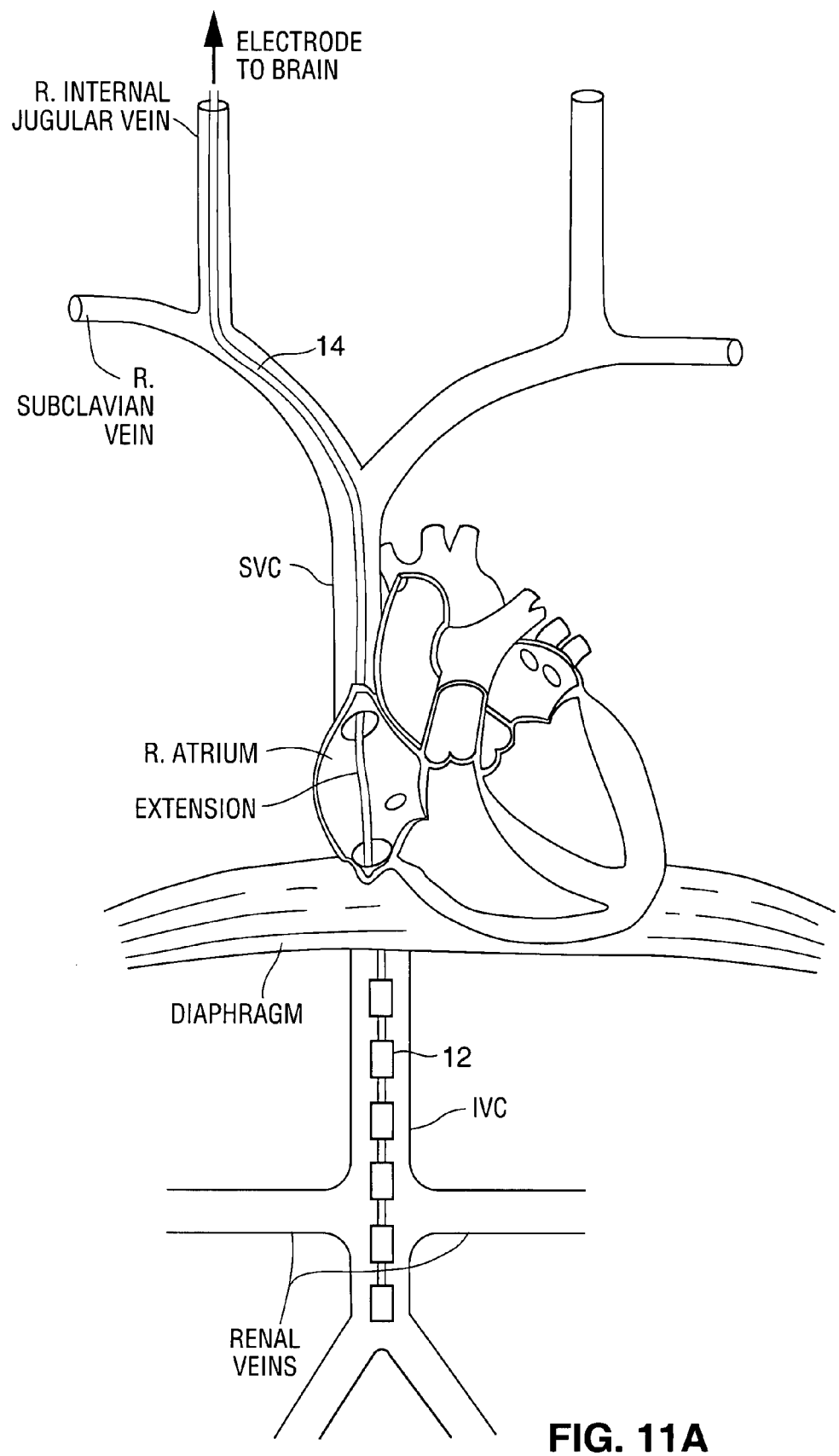
Figure 11B:
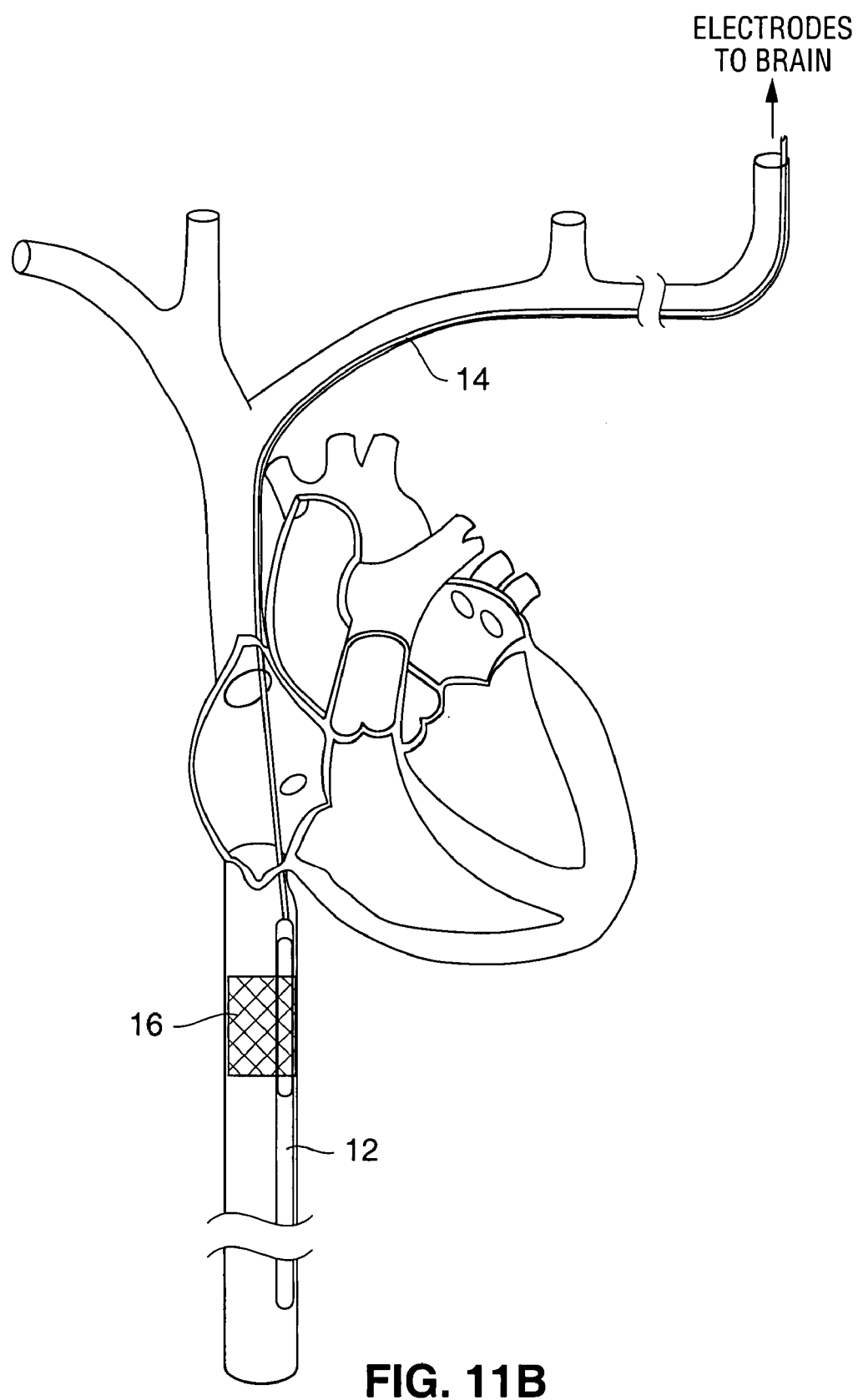

In another treatment which may be used for sleep apnea or other conditions for which deep brain stimulation is suitable (e.g. epilepsy), lead 14 may be extended into the brain (for example, as described in connection with FIG. 7) for deep brain stimulation as shown in FIG. 11A. Routes for passage of the lead into the brain include, but are not limited to, the facial vein and the retro-mandibular vein. FIG. 11B illustrates positioning of the device 12 in the inferior vena cava, with the lead 14 extending superiorly towards the brain.

Figure 12:
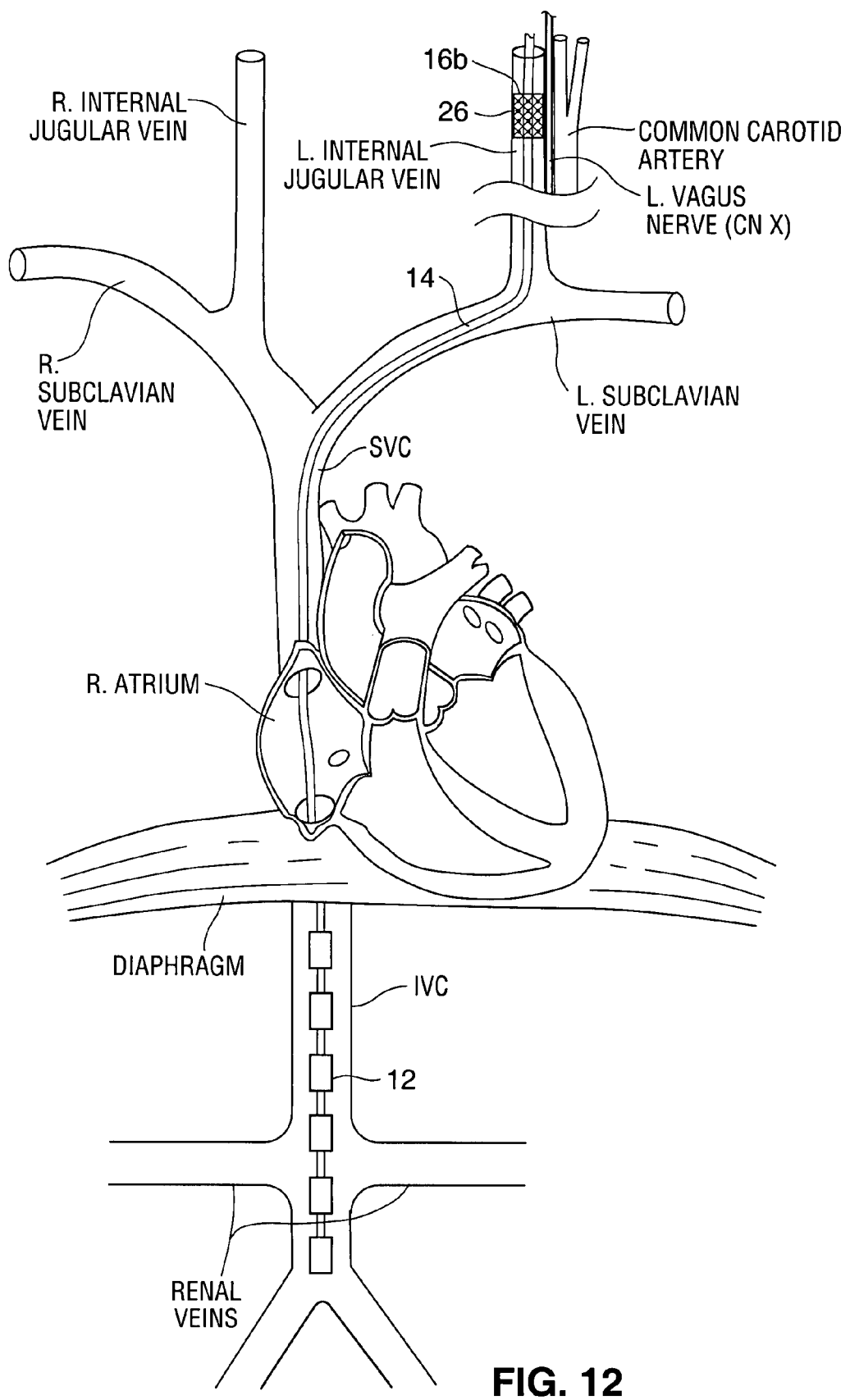
Figure 13:
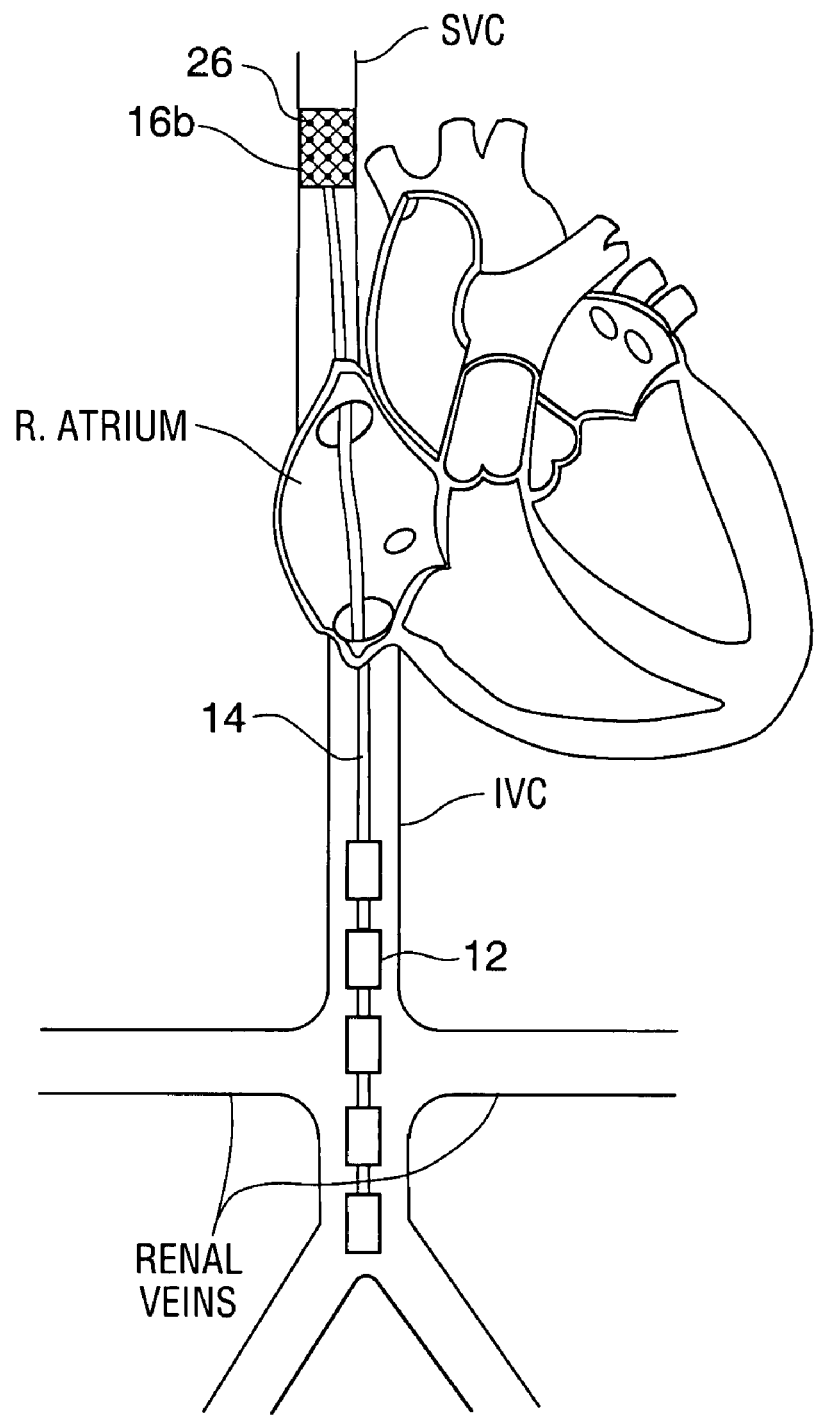

The disclosed system may be used to deliver vagus nerve stimulation for treatment of various diseases or conditions, including but not limited to epilepsy, depression, Alzheimer's disease, anxiety disorders (for example, obsessive compulsive disorder), tourette syndrome, bulimia, and obesity. The FIG. 12 embodiment illustrates positioning of stimulation electrodes in the internal jugular vein at a location from which energy from the electrodes can be conducted through the jugular vein to the left vagus nerve. Alternate electrode positions might also be used, including the superior vena cava and the brachio-cephalic veins, among others. Although FIG. 12 illustrates transvenous stimulation of the nerve, it should be appreciated that with any of the disclosed embodiments, direct stimulation may instead be employed by passing the lead through the vessel wall and positioning it in contact with the target neural structure.

Neurostimulation of cardiac parasympathetic nerves and plexuses may be used to treat multiple types of aberrant heart rates and rhythms. In one example shown in FIG. 13, of a neurostimulation system is used for ventricular rate control during atrial fibrillation. In this embodiment, the electrode is positioned within the superior vena cava or in an alternate location from which it can be used to stimulate adjacent cardiac parasympathetic nerves to achieve ventricular rate control during atrial fibrillation. Operating parameters may be selected to deliver high-frequency (e.g. on the order of 50-250 Hz) nerve stimuli during the atrial refractory period, thus preventing atrial excitation during the adjacent nerve stimulation.

Neurostimulation of cardiac parasympathetic nerves and plexuses may be accomplished either directly or transvenously, and may be performed at multiple sites, including but not limited to the superior vena cava, the inferior vena cava, and the coronary sinus.

Alternative Applications

Suitable applications for use of these devices/systems include, but are not limited to:

Deep brain stimulation (DBS) or cortical stimulation (alone or in combination with drug delivery to the stimulated area) for treatment of motor disorders including essential tremor, Parkinson's disease, Dystonia, for stroke rehabilitation, as well as other neurological disorders including obsessive conpulsive disorder, epilepsy, depression, mood disorders, anxiety disorders, pain and tinnitus. Stimulation might be delivered to regions of the brain (e.g. the insula) to control addiction to substances or behavior.

Occipital nerve stimulation (ONS) for treatment of headaches;

Vagus nerve stimulation (VNS) for treatment of epilepsy, depression, hypertension or heart failure;

Peripheral nerve stimulation (PNS) for treatment of chronic pain;

Spinal cord stimulation (SCS) (alone or in combination with drug delivery to the stimulated area) for treatment of chronic pain, angina pain, peripheral vascular disease pain, malignant pain, ALS symptoms, and symptoms of Huntington's disease;

Stimulation of nerves in the gastric system for obesity treatment and gastroparesis;

Sacral or pelvic nerve stimulation for treatment of incontinence, pelvic pain, and sexual dysfunction;

Stimulation of the pancreas to upregulate the production of insulin or the electroporation of islet cells in treatment of diabetes.

The devices disclosed might be used for non-neurological therapy as well, such as the use of internal electrical stimulus to promote healing of wounds on or within the body. For example, targeted sympathetic blockade or parasympathetic nerve stimulation may be used to increase regional blood flow in various target areas to promote ulcer healing in patients with peripheral vascular disease.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents. The terms "first," "second" and the like, where used herein, do not denote any order, quantity, or importance. In references to "first blood vessel", "second blood vessel" etc., the first and second blood vessels may be different blood vessels or they may be the same blood vessel unless otherwise specified.

Any and all patents, patent applications and printed publications referred to above are incorporated by reference.

We claim:

1. A method of electrically stimulating a nervous system target and delivering an agent into a blood vessel, the method comprising:

selecting a nervous system target to receive electrical stimulation;

introducing a neurostimulation implant including a pulse generator into the vasculature of a patient and advancing the neurostimulation implant to a first blood vessel;

retaining the neurostimulation implant within the first blood vessel; and positioning at least one electrode within the patient, the electrode in communication with the neurostimulation implant, and stimulating the nervous system target using the electrode;

providing an intravascular drug delivery implant comprising a reservoir;

introducing the drug delivery implant into a second blood vessel;

retaining the drug delivery implant within the second blood vessel; and releasing agent from the reservoir into the cardiovascular system.

2. The method according to claim 1, wherein the neurostimulation implant includes the reservoir.

3. The method according to claim 1, wherein the neurostimulation implant is electronically coupled to the drug delivery implant.

4. The method according to claim 1, wherein the neurostimulation implant is in wireless communication with the drug delivery implant.

5. The method of claim 1, wherein the drug delivery implant includes an elongate conduit extending from the reservoir, and the method includes positioning the conduit to release agent into a target region of the cardiovascular system.

6. The method of claim 5, wherein the target region of the cardiovascular system is a third blood vessel, and wherein the method includes positioning the conduit to release agent into the third blood vessel.

7. The method of claim 6, wherein the third blood vessel is a renal artery.

8. The method of claim 5, wherein the target region is an organ.

9. The method of claim 8, wherein the organ is the heart.

10. The method of claim 5, wherein the organ is a kidney.

11. The method according to claim 5, further including passing the conduit through a wall of the second blood vessel and positioning the conduit to release an agent into contact with the nervous system target.

12. The method according to claim 11, further including extending the conduit into tissue of the nervous system target.

* * * * *